United States Patent
Osborne et al.

(10) Patent No.: US 9,637,790 B2
(45) Date of Patent: May 2, 2017

(54) DETECTING MUTATIONS IN DNA

(75) Inventors: Adam E. Osborne, Waltham, MA (US); Lawrence J. Wangh, Auburndale, MA (US); John E. Rice, Quincy, MA (US)

(73) Assignee: Brandeis University, Waltham, MA (US)

( * ) Notice: Subject to any disclaimer, the term of this patent is extended or adjusted under 35 U.S.C. 154(b) by 606 days.

(21) Appl. No.: 13/991,022

(22) PCT Filed: Dec. 1, 2011

(86) PCT No.: PCT/US2011/062793
§ 371 (c)(1),
(2), (4) Date: Sep. 12, 2013

(87) PCT Pub. No.: WO2012/075230
PCT Pub. Date: Jun. 7, 2012

(65) Prior Publication Data
US 2013/0344484 A1    Dec. 26, 2013

Related U.S. Application Data

(60) Provisional application No. 61/419,575, filed on Dec. 3, 2010.

(51) Int. Cl.
*C12Q 1/68* (2006.01)

(52) U.S. Cl.
CPC ......... *C12Q 1/6883* (2013.01); *C12Q 1/6818* (2013.01); *C12Q 1/6827* (2013.01); *C12Q 1/6858* (2013.01)

(58) Field of Classification Search
USPC ...................... 435/6.12, 91.2, 800
See application file for complete search history.

(56) References Cited

U.S. PATENT DOCUMENTS

| | | | |
|---|---|---|---|
| 7,198,897 B2 | 4/2007 | Wangh et al. | |
| 7,915,014 B2 | 3/2011 | Wangh et al. | |
| 2004/0229253 A1* | 11/2004 | Hyldig-Nielsen | ... C12Q 1/6818 435/6.12 |

(Continued)

FOREIGN PATENT DOCUMENTS

| | | |
|---|---|---|
| EP | 1468114 | 5/2008 |
| EP | 2248915 | 11/2010 |

(Continued)

OTHER PUBLICATIONS

Afonina et al., "Primers with 5' flaps improve real-time PCT," Biotechniques, Informa Healthcare, 2007, 43(6).

(Continued)

*Primary Examiner* — Stephanie K Mummert
(74) *Attorney, Agent, or Firm* — Foley Hoag LLP

(57) ABSTRACT

Provided herein are methods for detecting mutations in nucleic acid, and compositions and kits for performing such methods. In particular, nucleic acid amplification and fluorescence detection methods are provided to detect mutations and assess the mutational load. The methods are based on a set of adjacently binding probes wherein one probe is labelled with a quencher and the other is a self-indicating probe labelled with fluorophore and quencher. The binding of the probes is analyzed by melting curve analysis.

15 Claims, 12 Drawing Sheets

(56) References Cited

U.S. PATENT DOCUMENTS

| | | | | |
|---|---|---|---|---|
| 2006/0194239 | A1* | 8/2006 | Parker | 435/6 |
| 2008/0193934 | A1* | 8/2008 | Wangh | 435/6 |

FOREIGN PATENT DOCUMENTS

| | | |
|---|---|---|
| EP | 1805199 | 1/2011 |
| WO | 03/054233 | 7/2003 |
| WO | 2009/135832 | 11/2009 |
| WO | 2011/050173 | 4/2011 |

OTHER PUBLICATIONS

Allawi and Santalucia, "Thermodynamics and NMR of internal G.T mismatches in DNA," 1997, Biochem. 36: 10581-10594.

Anderson et al., "Sequence and Organization of the Human Mitochondrial Genome." Nature, 1981, 290. pp. 457-465.

Andrews et al., "Reanalysis and revision of the Cambridge reference sequence for human mitochondrial DNA." Nature Genetics, 1999, 23. pp. 147.

Arnaudo et al., "Depletion of muscle mitochondrial DNA in AIDS patients with zidovudine-induced myopathy," Lancet, 1991, 337, 508-510.

Chen and Kadlubar, "Mitochondrial Mutagenesis and Oxidative Stress in Human Prostate Cancer." Journal of Environmental Science and Health, 2004, C22. pp. 1-12.

Cote et al., "Changes in mitochondrial DNA as a marker of nucleoside toxicity in HIV-infected patients," New England Journal of Medicine, 2002, 346(11), 811-820.

Fleischman et al., "Effects of a nucleoside reverse transcriptase inhibitor, stavudine, on glucose disposal and mitochondrial function in muscle of healthy adults," American Journal of Physiology-Endocrinology and Metabolism, 2007, 292, 1666-1673.

He et al., "Heteroplasmic mitochondrial DNA mutations in normal and tumour cells," Nature, 2010, vol. 464(7288): 610-614.

Huang et al., "Multiplex Fluorescense Melting Curve Analysis for Mutation Detection with Dual-Labeled, Self-Quenched Probes," PLOS ONE, 2011, 6(4): E19206.

International Search Report, International Patent Application No. PCT/US2011/062793, mailed Mar. 23, 2012, 4 pages.

Martin et al., "Accumulation of Mitochondrial DNA Mutations in Human Immunodeficiency Virus—Infected Patients Treated with Nucleoside-Analogue Reverse-Transcriptase Inhibitors," American Journal of Human Genetics, 2003, 72, 549-560.

Onyango et al., "Mitochondrial genomic contribution to mitochondrial dysfunction in Alzheimer's disease," Journal of Alzheimer's Disease, 2006, 9, 183-193.

Osborne, "Single-Molecule LATE-PCR Analysis of Human Mitochondrial Genomic Sequence Variations," PLOS ONE, vol. 4 (5): C5636.

Pierce et al., "Linear-After-The-Exponential (LATE)-PCR: Primer design criteria for high yields of specific single-stranded DNA and improved real-time detection," 2005, Proc. Natl. Acad. Sci. (USA) 102: 8609-8614.

Pravenec et al., "Direct Linkage of Mitochondrial Genome Variation to Risk Factors for Type 2 Diabetes in Conplastic Strains." Genome Research, 2007, 17. pp. 1319-1326.

Rice et al. "Monoplex/multiplex linear-after-the-exponential-PCR assays combined with PrimeSafe and Dilute-'N'-Go sequencing," Nature Protocols, 2007, 2 (10), 2429-2438.

Sanchez et al., "Linear-After-The-Exponential (LATE)-PCR: An advanced method of asymmetric PCR and its uses in quantitative real-time analysis," Proc. Nat. Acad. Sci. (USA), 2004, 101: 1933-1938.

Sanchez et al., "Two-temperature LATE-PRC endpoint genotyping," BMC Biotechnology, BioMed Central Ltd., 2006, 6(1): 44.

Santalucia, "A unified view of polymer, dumbbell, and oligonucleotide DNA nearest-neighborthermodynamics," PNAS (USA), 1998, 95(4): 1460-1465.

Swerdlow et al., "A 'Mitochondrial Cascade Hypothesis' for Sporadic Alzheimer's Disease" Medical Hypotheses, 2004, 63. pp. 8-20.

Wallace, "Mitochondrial DNA sequence variation in human evolution and disease." Proceedings of the National Academy of Science, 1994, 91. pp. 8739-8746.

Wendelsdorf et al., "An Analysis of Enzyme Kinetics Data for Mitochondrial DNA Strand Termination by Nucleoside Reverse Transcription Inhibitors," PLoS Comput Biol, 2009, 5(1): e1000261. doi:10.1371/journal.pcbi.1000261.

Wong et al., "Real-time quantitative polymerase chain reaction analysis of mitochondrial DNA point mutation," Methods in Molecular Biology, 2006, 335, pp. 187-200.

\* cited by examiner

FIG. 2A

<u>        SEQ ID NO.: 42        </u>
AAAGCGGTGTGTGTGTGCTGGGTA
GCTCGCCACACACACACGACCCATCCTACCCGCCCCCAACATAACTACTCTAATCATCAT

ACCCTCACCCTCCCCTTTTATTACACAATCAACCCCCCACTGACAATTTTCACGTATGGC

<u>         SEQ ID NO.: 75          </u>  QF <u>    SEQ ID NO.: 43        </u>  Q
           AATgTGAAATCTGcTTgGGCTGGTGTTAGGGTTCTTT_aTTTTGGGGTT
GGTTTTCTATTTTAAACTTTAGACCAATCCGACCACAATCCCAAGAAACAAAAACCCCAA

Q  <u>  SEQ ID NO.: 44       </u>     FQ<u>    SEQ ID NO.: 45            </u>
TGGCAGAGATGTcTTTAAGTGCTGTGGCtAGgAGttGGGGAGGGcGGGTTTGGgGGAAgT
ACCGTCTCTACACAAATTCACGACACCGGTCTTCGCCCCCTCCCCCCCAAACCACCTTTA

<u> SEQ ID NO.: 45 </u>  QF <u>  SEQ ID NO.: 46            </u>  Q
TTTTTcTTATtATGTCTGgGTGaAAAGTGaCTaTGCgGAC
AAAAACAATACTACAGACACACCTTTCACCGACACGTCTGTAAGTTAACAATAATAATAC

<u>                SEQ ID NO.: 47            </u>  QF <u> SEQ ID NO.: 48 </u>
                TTTAGTAAaTgTGTTCaCCTGTAATATTGAAC
AGGATGTTCGTAATTAATTAATTGTGTGAAATCATTCATACAAGCGGACATTATAACTTG

<u>  SEQ ID NO.: 48       </u>  Q
aTAGGTaCGATAAATAAT
CATCCACGCTATTTATTATCCTACTCCGTCCTTAGTTTCTGTCTATGACGCTGTATCCCA

Q <u>   SEQ ID NO.: 49         </u>  FQ<u> SEQ ID NO.: 50 </u>
           AATGtaATCGCGTtCATAtCaCCCAGACGAgAgTACCcA
CGAGGCCGAGGTCGCAGAGCGTTACGATAGCGCACGTATGGGGGGTCTGCTTTTATGGTT
<u>SEQ ID NO.: 50</u>
AcGCATGGAGAG
TACGTACCTCTCGAGGGCACTCACCAATTATCCCACTATCTGGACACTAGGTAGCACTAC

AGAATAAATTCCCCTTGCACACCCGATAAATCCGAAATACTGGGACTTCA

FIG. 2B

```
              SEQ ID NO.: 51
       AATAGAGGGGGTAGAGGGGGTGCTATAGGGT
CCCGAGATCTCCCCCATCTCCCCCACGATATCCCATTTATGCCCGGGATAAAGTTTCTAA

AAATCCCCTTAATTAAGATCCTGCTACCCGTACTTTGACACCAAACGAGGTGTCTAAAGT
            Q   SEQ ID NO.: 52       FQ    SEQ ID NO.: 53              Q  SEQ ID NO.: 54
            TGACCaTAaTATACCtCCGGTCGTaTAGtGGTcAAtGTGGTaTGGTTTAtACGT
CTCGTAACTGGCATCATATGGGGGCCAGCACATCGCCACTTTCACCAAACCAAATCTGCA
      SEQ ID NO.: 54    FQ  SEQ ID NO.: 55                        SEQ ID NO.: 56
      aCGGcAATTaCATCTGTTTTTAAattTAATaTGGGGAtAGC                   AGACGTCT
GGCCCTTAACGTAGACAAAAATTCGGATTACACCCCTGTCGAGTACTCACGTTCTGCAGA SEQ ID NO.: 56      QF    SEQ ID NO.: 57          QQ   SEQ ID NO.: 58
     TaTGtTGTAATTATTATACGAtTGGGGaCTTtAATtGGGAGTACTACTCGATTaTCAACG
ACACTACATTAATAATATGCTTACCCCCGAAGTTAGCCCTCATGATGAGCTAACAGTTGC SEQ ID NO.: 58  FQ       SEQ ID NO.: 59        Q    SEQ ID NO.: 60             FQ  SEQ ID NO.: 61
                TCAAGGAGTCGCAGGaCGCCTaGTTCTAGGAA AATGGGGGAAGTtTGTtGGAGTTGAAG
AGTTCCTCAGCGTCCAGCGGACCAAGATCCTTATTACCCCCTTCATACATCCTCAACTTC
        SEQ ID NO.: 61
ATaAGTtCGCtGTAttCGGTGT
TAATCAGGCGGCATCAGCCACATGAGCATCCAAGTCATGGTAACCACCGGTTAACTAAAC
              SEQ ID NO.: 62             QF    SEQ ID NO.: 63             Q
              GAGGcATtGTTcACgTCGTtTGTTATGTAAAGaATGCGTAGaGATaGGAG
TACCATTCCCTCCCTAGCAACTGGAGCAGACAATACATTTCCTACGCATCCCTACCCTCC

CGCTACTCCTGATCCTACTACCGCCCGTCCTATCAAGTCTGCCAAAGATAAAGGACTCGC

AGACTCTACAATCATAATCAATCAAAACAACACTCACAATCCTTTTCCCGTATGTCCTGA

TCCTTCGTCTATTCCT
```

FIG. 2C

```
                                                                    SEQ ID NO.: 64
                                                                         AA
AAAAAAGTATCCTCCACATACTCAACCAGCATCGCCTTAGCCCCCATACGACAAGCTTAA
                SEQ ID NO.: 64
CATAAGAACAGGGAGGTTAGAAGTAGGGTCTTGGT
GTATTCTTGTCCCTCCAATCTTCATCCCAGAACCACTGTTTTATACAACACATCTCAAGT

Q      SEQ ID NO.: 65          FQ SEQ ID NO.: 66
                                    AAGgTTGTAGTGaTGgGGGTGTTTATTATA
CCCCTCTCACGCAGTATACAACAAGGATCCTTCTAACATCACCACTCCCACAAATAATAT

SEQ ID NO.: 66            Q    SEQ ID NO.: 67          FQ  SEQ ID NO.: 68
ATAATcTTTGTGTtTTCGGCTATGAAGAATAGaGCGAAGaGGCCTGCGGCcTATTCcATG
TATTACAAACACATAAGCCGATACTTCTTATCCCGCTTCCCCGGACGCCGCATAAGCTAC

SEQ ID NO.: 68                       SEQ ID NO.: 69       QF SEQ ID NO.: 70
   TTGAcGCCTG                     TTCGGCAAtGTCGAgGGGGGTTCGGTTGGTt
AACTTCGGACTCTGATCAAGCCTGAGGGGAAGCCGTTCCAGCTTCCCCCAAGCCAACCAG

SEQ ID NO.: 70   QQ       SEQ ID NO.: 71       FQ     SEQ ID NO.: 72
TtTGCTgGTGTGGAGATAAAcCATAgTATGtCCgAGGGTCATGATtGCAGtAGTggTaAG
AGACGATCACACCTCTATTTAGTATAATACCGGTTCCCAGTACTACCGTCCTCATTAGTC
SEQ ID NO.: 72
      AGG
   TCCACAAGAACACAACACTATTCCCACCTCTCCAATTTCCTCGGTGAATAATCATTACAA

CTATCATCTTACTACCGATCCCACTGAAGTATACTCTAACAAACCCGATGACGAGCGTCA

CGCGGCTAGTCCCGCATCAAACTCAAACTACGAGTGGGACTAGTCTCCTAACTCATTTGC

Q SEQ ID NO.: 73
                                                      TTGAtCAaGGGGTTt
   CGATCCGATCTCCACCGATCTTATTTATCCTCCGGATCCAACTCCAACTGGTCCCCCAAC

SEQ ID NO.: 73   FQ    SEQ ID NO.: 72
   GGTATaGGGAGGGaGGTTtATAGTAaAAGAGaGAT
   CCATACCCCTCCCCCCAAGTATCATCTTCTCGCTACCACTCTCGATTCCAGCCCCGC
```

DETECTING MUTATIONS IN DNA

CROSS-REFERENCE TO RELATED APPLICATIONS

The present invention claims priority to U.S. Provisional Patent Application Ser. No. 61/419,575, filed Dec. 3, 2010, which is incorporated by reference in its entirety.

FIELD OF THE INVENTION

Provided herein are methods for detecting mutations in nucleic acid, and compositions and kits for performing such methods. In particular, nucleic acid amplification and fluorescence detection methods are provided to detect mutations and assess the mutational load.

BACKGROUND

Mitochondria are the primary energy source of most eukaryotic cells. Each mitochondrion possesses multiple copies of mitochondrial DNA (mtDNA). The human mitochondrial genome is a closed circular molecule of DNA 16 kb long. It encodes genes for 13 electron transport chain proteins, 22 tRNAs, and two rRNAs. The mitochondrial genome also includes a control region that contains the displacement loop (D-Loop), within which DNA replication is initiated and gene transcription is regulated. By convention, one particular sequence, known as the revised Cambridge Reference Sequence (rCRS), or the Anderson sequence, serves as a reference sequence to which the other sequences are compared (Anderson et al. (1981) Nature 290, 457-465.; Andrews et al. (1999) Nature Genetics 23, 147.; herein incorporated by reference in their entireties). Recently, increased levels of mutations within the mitochondrial genome have been linked to several diseases, including diabetes, Alzheimer's, and cancer (Wallace (1994) Proceedings of the National Academy of Science, 91, 8739-8746.; Pravenec et al. (2007) Genome Research, 17, 1319-1326.; Swerdlow (2004) Medical Hypotheses, 63, 8-20.; Chen et al. (2004) Journal of Environmental Science and Health, C22. pp. 1-12.; herein incorporated by reference in their entireties). Despite these insights a substantial technical challenge persists in the areas of detecting, characterizing, and diagnosing changes in mtDNA sequence largely because there are very large numbers, tens to many thousands, of mtDNA molecules in each eukaryotic cell. This means that changes in mtDNA molecules are often "averaged out" in populations of mtDNA molecules, even in single cells. What is needed are better systems and methods for characterizing mtDNA to assist in biological research, drug development, assessment and monitoring of drug or therapeutic impact, and disease screening, diagnosis, and monitoring.

SUMMARY

In some embodiments, provided herein are methods for detecting mutations in nucleic acids (e.g. RNA, DNA (e.g. genomic DNA, non-genomic DNA (e.g. chloroplastic DNA ("cpDNA"), mitochondrial DNA, episomal DNA, plasmid DNA, viral nucleic acid, bacterial, nucleic acid, methylated stretches of nucleic acid, etc.))). Any type of target nucleic acid may be employed to find unanticipated mutations using the methods and compositions herein.

In some embodiments, provided herein are methods for detecting mutations in nucleic acid (e.g., mtDNA, cpDNA, or other nucleic acid), comprising one or more or all of the following steps: (a) providing: (i) a sample comprising nucleic acid (e.g., mtDNA or cpDNA), and (ii) detection reagents comprising at least one pair of primers configured to amplify a target region of said nucleic acid, and at least one detectably distinguishable probe set of two hybridization probes which hybridize to adjacent sequences in said target region, each probe set comprising: (A) a quencher probe labeled with a non-fluorescent quencher, and (B) a signaling probe labeled with a fluorescence-emitting dye and a non-fluorescent quencher, wherein the signal probe does not emit fluorescence above background when not hybridized to its target sequence, but emits a fluorescence signal above background level of the no-template control upon hybridization to its target sequence in the absence of bound adjacent quencher probe and below background upon hybridization to its target sequence in the presence of bound adjacent quencher probe, wherein, if both signaling and quencher of the probe pair are hybridized to their adjacent target nucleic acid sequences, the non-fluorescent quencher of the quencher probe of the adjacent probe quenches the signal from the signaling probe of the adjacent probe; (b) amplifying the target region of said nucleic acid (e.g., mtDNA or cpDNA) with the primers; (c) detecting the fluorescence of the fluorescence-emitting dye from each detectably distinguishable probe set at a range of temperatures; (d) generating temperature-dependent fluorescence signatures for each fluorescence-emitting dye; and (e) analyzing the temperature-dependent fluorescence signatures to detect mutations in said nucleic acid (e.g., mtDNA or cpDNA).

In some embodiments, provided herein are reagent kits for detecting one or more mutations in a target region of mtDNA, cpDNA, or other nucleic acid, comprising one or more or all of: (a) at least one pair of primers, wherein said primers are configured bind to and amplify the target region of mtDNA, cpDNA, or other nucleic acid; and (b) at least one detectably distinguishable probe set of two hybridization probes which hybridize to adjacent sequences within the target region of mtDNA, cpDNA, or other nucleic acid, comprising: (i) a quencher probe labeled with a non-fluorescent quencher, and (ii) a signaling probe labeled with a fluorescence-emitting dye and a non-fluorescent quencher, wherein the signal probe, when not hybridized to its target sequence, does not emit fluorescence above background level of fluorescence observed in the absence of a template, but emits a fluorescence signal above the background level fluorescence upon hybridization to its target sequence in the absence of bound quencher probe, or emits a fluorescence signal below the background level of fluorescence upon hybridization to its target sequence in the presence of the bound quencher probe, wherein, if both signaling and quencher probes are hybridized to their adjacent target nucleic acid sequences, the non-fluorescent quencher of the quencher probe quenches the signal from the signaling probe.

In some embodiments, the concentration of the quencher probe is higher than the concentration of the associated signaling probe in a probe set. In some embodiments, the melting temperature of the signaling probe in a probe set is higher than the melting temperature of the associated quencher probe. In some embodiments, the melting temperature of the signaling probe in a probe set is the same, or about the same, as the melting temperature of the associated quencher probe. In some embodiments, the melting temperature of the signaling probe in a probe set is lower than the melting temperature of the associated quencher probe. In some embodiments, the quencher probe and/or signaling probe are configured to hybridize to regions of mtDNA which are prone to mutational buildup (e.g., buildup over time or in response to drugs, environmental exposures, or other causes). In some embodiments, the fluorescence-emitting dye and said non-fluorescent quenchers of each probe set are capable of interacting by FRET. In some embodiments, the detection reagents comprise two or more probe sets. In some embodiments, the two or more probe sets comprise different fluorescence-emitting dyes that emit at detectably different wavelengths. In some embodiments, the two or more probe sets comprise the same fluorescence-emitting dyes. In some embodiments, probe sets comprising the same fluorescence-emitting dyes hybridize to their target nucleic acid sequences at detectably different melting temperatures with their target nucleic acid sequences. In some embodiments, each of said two or more probe sets are detectably distinguishable from all other probe sets in said detection reagents by (1) melting temperature, (2) emission wavelength of said fluorescence-emitting dye, or (3) a combination thereof. In some embodiments, the detection reagents comprise five or more probe sets. In some embodiments, the detection reagents comprise primers and probes for two or more non-overlapping target regions. In some embodiments, the detection reagents comprise one or more probe sets for each target region. In some embodiments, the detection reagents comprise five or more probe sets for each target region.

In some embodiments, the degree of complemetarity between the probes of said probe sets and their target sequence varies based on the number of mutations in said target sequence. In some embodiments, the different degrees of complementarity result in different temperature-dependent fluorescent signatures generated by the probe set and the target sequences. In some embodiments, the different temperature dependent fluorescent signatures are used to detect mutations in the target sequences. In some embodiments, the different temperature dependent fluorescent signatures are used to assess the mutational load (i.e., the absolute or relative number of mutations) of said target sequence. In some embodiments, the different temperature dependent fluorescent signatures are used to quantify the mutational load of said target sequence. In some embodiments, mutational load is used to assess increased risk for one or more diseases. In some embodiments, mutational load is used to detect or diagnose one or more diseases. In some embodiments, mutational load is used to assess the impact of a treatment of other type of exposure on a subject. In some embodiments, the temperature-dependent fluorescence signature comprises a melt curve or an annealing curve. In some embodiments, the analyzing the temperature-dependent fluorescence signature comprises comparison to a previously established melting curve or annealing curve. In some embodiments the previously established melting curve or an anneal curve is a consensus or bulk curve established using a mixture containing more that 100 mtDNA molecules (or cpDNA molecules), while the fluorescence signature to which it is compared is generated from 10 or fewer mtDNA molecules (or cpDNA molecules). In some embodiments, mutational load is used to detect or diagnose or monitor progression of one or more diseases. In some embodiments, the analyzing is performed by a computer. In some embodiments, amplification is by a non-symmetric amplification method that includes extension of primers and a mean primer annealing temperature after the first few amplification cycles. In some embodiments, amplification is a LATE-PCR amplification. In some embodiments, the probes in the at least one detectably distinguishable probe set have melting temperatures with their target nucleic acid sequences below the annealing temperature of at least one primer of the amplification reaction.

In some embodiments, one or more detectably distinguishable probe sets are configured to hybridize to the HV2 region of mtDNA. In some embodiments, detectably distinguishable probe sets are selected from one or more of: (a) SEQ ID NO:10 and SEQ ID NO:11; (b) SEQ ID NO:12 and SEQ ID NO:13; (c) SEQ ID NO:14 and SEQ ID NO:15; (d) SEQ ID NO:16 and SEQ ID NO:17; and (e) SEQ ID NO:18 and SEQ ID NO:19.

In some embodiments, one or more primer pairs are configured to amplify all or a portion of said HV2 region of mtDNA. In some embodiments, one or more primer pairs comprise SEQ ID NO.:1 and SEQ ID NO.:2. In some embodiments, one or more detectably distinguishable probe sets are configured to hybridize to the CO2 region of mtDNA. In some embodiments, detectably distinguishable probe sets are selected from one or more of: (a) SEQ ID NO:20 and SEQ ID NO:21; (b) SEQ ID NO:22 and SEQ ID NO:23; (c) SEQ ID NO:24 and SEQ ID NO:25; (d) SEQ ID NO:26 and SEQ ID NO:27; (e) SEQ ID NO:28 and SEQ ID NO:29; and (f) SEQ ID NO:30 and SEQ ID NO:31 or variants thereof.

In some embodiments, one or more primer pairs are configured to amplify all or a portion of said CO2 region of mtDNA. In some embodiments, one or more primer pairs comprise SEQ ID NO.:3 and SEQ ID NO.:4 or variants thereof. In some embodiments, one or more detectably distinguishable probe sets are configured to hybridize to the ND1 region of mtDNA. In some embodiments, detectably distinguishable probe sets are selected from one or more of: (a) SEQ ID NO:32 and SEQ ID NO:33; (b) SEQ ID NO:34 and SEQ ID NO:35; (c) SEQ ID NO:36 and SEQ ID NO:37; (d) SEQ ID NO:38 and SEQ ID NO:39; and (e) SEQ ID NO:40 and SEQ ID NO:41 or variants thereof.

In some embodiments, one or more primer pairs are configured to amplify all or a portion of said ND1 region of mtDNA. In some embodiments, one or more primer pairs comprise SEQ ID NO.:5 and SEQ ID NO.:6 or variants thereof. In some embodiments, detecting mutations in mtDNA comprises detecting mutations in one or more of the HV2, CO2, and ND1 regions of mtDNA. In some embodiments, detecting mutations in mtDNA comprises detecting mutations in the HV2, CO2, and ND1 regions of mtDNA.

In some embodiments, reagent kits may comprise probe sets, primers, amplification reagents (e.g. amplification buffer, DNA polymerase, control reagents (e.g., positive and negative controls)) or any other components that are useful, necessary, or sufficient for practicing any of the methods described herein, as well as instructions, analysis software (e.g., that facilitates data collection, analysis, display, and reporting), computing devices, instruments, or other systems or components. In some embodiments, additional oligonucleotides are configured to suppress mis-priming during amplification reactions. In some embodiments, additional oligonucleotides are configured to disrupt structural elements within target nucleic acid sequences during amplification reactions or during probing of amplified sequences.

In some embodiments, signaling probes comprise quenched fluorophores. In some embodiments, the melting temperature of the signaling probe in a probe set is higher than the melting temperature of an associated quenching probe. In some embodiments, the melting temperature of the signaling probe in a probe set is the same, or about the same, as the melting temperature of the associated quencher probe. In some embodiments, the melting temperature of the signaling probe in a probe set is lower than the melting temperature of the associated quencher probe.

In some embodiments, methods provided herein are performed in a single reaction vessel. In some embodiments, methods provided herein are performed in single-vessel (e.g., tube, well, etc.) assays to detect mutations in mtDNA target sequence or sequences. In some embodiments, a sample of target sequence in single-stranded form is generated by an amplification method that generates single-stranded amplicons, for example, a non-symmetric polymerase chain reaction (PCR) method, most preferably LATE-PCR. In some embodiments, only a few pairs of primers are used, generally not more than three pairs, preferably not more than two pairs and more preferably only a single pair of primers that hybridizes to the sequences flanking a target sequence. In some embodiments, assays using multiple target sequences (e.g. 2, 3, 4, 5, 6, 7, 8, 9, 10, etc.) utilize a corresponding number of primer pair sets (e.g. 2, 3, 4, 5, 6, 7, 8, 9, 10, etc.). In some embodiments, the primers and at least one set of signaling and quencher probes (e.g., two sets, three sets, etc.) for each target sequence are included in the amplification reaction mixture.

In some embodiments, probe sets (e.g. signaling and quencher probes) are configured to hybridize to an mtDNA sequence (e.g. in a single sample). In some embodiments, probes hybridize with different Tm to the mtDNA of differing sequences (e.g. mtDNA containing one or more mutations). In some embodiments, one or both probes of a probe set (e.g. signaling and/or quencher probes) comprise different degrees of complementarity to mtDNA target sequences (e.g. different degrees of complementarity to the Anderson Sequence). In some embodiments, a signaling probe and/or quencher probe is configured to hybridize to mtDNA sequences containing mutations, mutations from wild-type mtDNA, mutations from the expected sequences of mtDNA, mutations from the consensus sequence generated from many (more than 100) molecules of mtDNA. In some embodiments, a signaling probe and/or quencher probe is configured to hybridize to mtDNA sequences containing mutations (i.e., the probe contains a corresponding nucleotide complementary to the mutation). In some embodiments, a signaling probe and/or quencher probe is configured to hybridize to mtDNA sequences containing mutations with different Tm than to consensus or wild-type target sequence. In some embodiments, a signaling probe is configured to hybridize to an mtDNA target sequence, with or without mutations. In some embodiments, a quencher probe is configured to hybridize to an mtDNA target sequence, with or without mutations.

In some embodiments, primers and probes are provided for use in the methods provided herein. In some embodiments, primers provided herein include: SEQ ID NOs: 1, 2, 3, 4, 5, 6, portions thereof, and sequences complementary thereto. In some embodiments, primers provided herein include oligonucleotides with 70% or greater sequence identity with SEQ ID NOs: 1, 2, 3, 4, 5, 6 (e.g. an oligonucleotide with 70% . . . 75% . . . 80% . . . 90% . . . 95% . . . 98% . . . 99% sequence identity), portions thereof, and sequences complementary thereto. In some embodiments, primers are provided that function substantially similarly to primers provided herein. In some embodiments, probes provided herein include: SEQ ID NOs: 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, portions thereof, and sequences complementary thereto. In some embodiments, probes provided herein include oligonucleotides with 70% or greater sequence identity with SEQ ID NOs: 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, portions thereof, and sequences complementary thereto. In some embodiments, probes are provided that function substantially similarly to probes provided herein. In some embodiments, target sequences for primers and probes provided herein comprise: SEQ ID NOs:7, 8, 9, portions thereof, and sequences complementary thereto. In some embodiments, target sequences comprise sequences 70% or greater sequence identity with SEQ ID NOs: 7, 8, 9, portions thereof, and sequences complementary thereto. In some embodiments, target sequences comprise regions of mtDNA. In some embodiments, target sequences comprise regions of mtDNA comprising the HV2 sequence. In some embodiments, target sequences comprise regions of mtDNA comprising the CO2 sequence. In some embodiments, target sequences comprise regions of mtDNA comprising the ND1 sequence. In some embodiments, probe and primer sequences are provided that hybridize or are configured to hybridize to sequences with 70% or greater sequence identity with SEQ ID NOs: 7, 8, 9, portions thereof, or sequences complementary thereto.

In some embodiments, probing and analysis methods provided herein apply to samples containing single-stranded mtDNA target sequences. Methods include analysis of a single sequence, analysis of two or more sequences in the same strand, analysis of sequences in different strands, and to combinations of the foregoing. A single-stranded nucleic acid target sequence may be a control sequence added to a sample. A nucleic acid target sequence may be DNA, cDNA, RNA, or any mixture of these types of nucleic acids. Said DNA, cDNA, RNA may come from any source. For example, it may occur naturally, or the target sequence may occur in double-stranded form, in which case the single-stranded target sequence is obtained by strand separation and purification. If the single-stranded nucleic acid target sequence is a cDNA sequence, it is obtained from an RNA source by reverse transcription.

In some instances, a target sequence is not available in sufficient copy number for probing and analysis (e.g. when obtained from a natural source or a forensic sample). In such instances the single-stranded target sequence is obtained by amplification, generally an amplification method that includes exponential amplification. In some embodiments an amplification reaction generates the single-stranded nucleic acid target sequence directly. In some embodiments an amplification reaction generates the target sequence in double-stranded form, in which event the single-stranded target sequence is obtained by strand separation and purification. Useful amplification methods that may be employed include, the polymerase chain reaction (PCR), including symmetric PCR, asymmetric PCR and LATE-PCR, any of which can be combined with reverse transcription for amplifying RNA sequences, NASBA, SDA, TMA, and rolling circle amplification. If the single-stranded nucleic acid target sequence is a cDNA sequence, the amplification method will include reverse transcription, for example, RT-PCR. In some embodiments, when non-symmetric amplification is utilized (e.g. LATE-PCR), probe sets are included in the amplification reaction mixture prior to amplification to avoid contamination.

In some embodiments, probe sets useful in methods provided herein include a signaling probe and an associated quencher probe. The signaling probe is a hybridization probe that emits a detectable signal, preferably a fluorescent signal, when it hybridizes to a single-stranded nucleic acid target sequence in a sample, wherein the signal is quenchable by the associated quencher probe. The quencher probe does not emit visible light energy. Generally, a signaling probe has a covalently bound fluorescent moiety. Signaling probes include probes labeled with fluorophores or other fluorescent moieties, for example, quantum dots. In some embodiments, fluorophore-labeled probes are preferred. One type of signaling probe is a ResonSense® probe. A ResonSense® probe is a single-stranded oligonucleotide labeled with a fluorophore that accepts fluorescence from a DNA dye and reemits visible light at a longer wavelength. Use of a ResonSense® probe involves use of a double-stranded DNA dye, a molecule that becomes fluorescent when it associates with double-stranded DNA, which in this case is the hybrid formed when the probe hybridizes to the single-stranded nucleic acid target sequence. For use of a ResonSense® probe, a DNA dye, for example, SYBR Green or SYBR Gold, is included in the sample containing the single-stranded nucleic acid target sequence along with the probe set or sets. Analysis includes exciting the dye and detection emission from the ResonSense® probe or probes. Unbound signaling probes need not be removed, because they are not directly excited and remain single-stranded. In some embodiments, preferred signaling probes are quenched probes; that is, probes that emit little or no signal when in solution, even if stimulated, but are unquenched and so emit a signal when they hybridize to a single-stranded nucleic acid sequence in a sample being analyzed. Yin-yang probes are quenched signaling probes. A yin-yang probe is a double-stranded probe containing a fluorophore on one strand and an interacting non-fluorescent quencher on the other strand, which is a shorter strand. When a yin-yang probe is in solution at the detection temperature, the fluorophore is quenched. The single-stranded nucleic acid target sequence out-competes the quencher-labeled strand for binding to the fluorophore-labeled strand. Consequently, the fluorophore-labeled strand hybridizes to the single-stranded nucleic acid target sequence and signals. Signaling probes for some embodiments provided herein are molecular beacon probes, single-stranded hairpin-forming oligonucleotides bearing a fluorescer, typically a fluorophore, on one end, and a quencher, typically a non-fluorescent chromophore, on the other end. In some embodiments, provided herein are single stranded oligonucleotides with any suitable type of secondary structure, bearing a fluorescence-emitting dye on one end and a quencher on the other end (molecular-beacon-type probes). Various signaling probes for use in embodiments herein comprise varying degrees of secondary structure (e.g. different lengths of hairpin (e.g. 2 base pairs, 3, base pairs, 4 base pairs, 5 base pairs, etc.). When molecular beacon probes, and other similar types of probes, are in solution, they assume a conformation wherein the quencher interacts with the fluorescer, and the probe is dark (e.g. hairpin conformation, closed conformation). When the probe hybridizes to its target, however, it is forced into an open conformation in which the fluorescer is separated from the quencher, and the probe signals.

In quenched signaling probes, quenching may be achieved by any mechanism, typically by FRET (Fluorescence Resonance Energy Transfer) between a fluorophore and a non-fluorescent quenching moiety or by contact quenching. In some embodiments, preferred signaling probes are dark or very nearly dark in solution to minimize background fluorescence. Contact quenching more generally achieves this objective, although FRET quenching is adequate with some fluorophore-quencher combinations and probe constructions.

The quencher probe of a probe set comprises or consists of a nucleic acid strand comprising a non-fluorescent quencher. In some embodiments, the quencher is, for example, a non-fluorescent chromophore such a dabcyl or a Black Hole Quencher (Black Hole Quenchers, available from Biosearch Technologies, are a suite of quenchers, one or another of which is recommended by the manufacturer for use with a particular fluorophore). In some embodiments, preferred quenching probes include a non-fluorescent chromophore. In some embodiments, quenchers are Black Hole Quenchers. The quencher probe of a set hybridizes to the single-stranded nucleic acid target sequence adjacent to or near the signaling probe such that when both are hybridized, the quencher probe quenches, or renders dark, the signaling probe. Quenching may be by fluorescence resonance energy transfer (FRET) or by touching ("collisional quenching" or "contact quenching").

FIG. 3 depicts the functioning of a generic set of probes binding to a generic target. In this embodiment there are two probe sets, probes 2, 4 and probes 6, 8. Probe 2 is a signaling probe, a molecular-beacon-type probe bearing fluorophore 3. Probe 6 is also a signaling probe, a molecular-beacon-type probe bearing fluorophore 7. Fluorophores 3, 7 are the same. Probes 4, 8 are quencher probes labeled only with Black Hole Quenchers 5 and 9, respectively. The melting temperatures (Tm's) of the probe-target hybrids (probes hybridized to single-stranded nucleic acid target sequence 1) are as follows: Tm probe 2>Tm probe 4>Tm probe 6>Tm probe 8. As the temperature of the sample is lowered from a high temperature at which no probes are bound, probes 2, 4, 6 and 8 bind to single-stranded nucleic acid target sequence 1 according to their hybridization characteristics. Probe 2, a signaling probe, binds first. FIG. 3, Panel B depicts probe 2 hybridized to sequence 1. As the temperature of the sample continues to be lowered, quencher probe 4 binds next, adjacent to probe 2 such that quencher 5 and fluorophore 3 are near to one another or touching. FIG. 3, Panel C depicts probe 4 hybridized to single-stranded nucleic acid sequence 1 adjacent to probe 2. At this point probe 2 is dark, or at least nearly dark. If, however, signaling probe 6 has begun to bind, it will emit fluorescence independently of probes 2, 4. FIG. 3, Panel D depicts probe 6 hybridized to single-stranded target sequence 1 adjacent to probe 4. Finally as the temperature continues to be lowered, probe 8 will bind, and its quencher 9 will quench fluorescence emission from fluorophore 7 of probe 6. FIG. 3, Panel E depicts probe 8 hybridized adjacent to probe 6. FIG. 3 Panel F line 11 depicts the gradual temperature dependent decrease in background signal due to unbound signaling probes in the absence of a target sequence. FIG. 3 Panel F line 10 depicts the temperature dependent increases and decreases in the fluorescent signal that arises as various probe-target hybrids form or melt in the presence of a target. The increase and decrease of fluorescence arises from fluorophores 3, 7. Such curves can be obtained as annealing (hybridization) curves as the temperature is lowered, or can be obtained as melting curves as the temperature is increased. As the sample temperature is lowered from 70° C., fluorescence curve 10 in Panel F first rises as probe 2 hybridizes to single-stranded nucleic acid sequence 1, then decreases as probe 4 binds, then increases again as probe 6 hybridizes, and finally decreases to the very low background level as probe 8 hybridizes and quenches all signal from its adjacent fluorophore 7 covalently linked to probe 6. One can deduce from curve 10 that each signaling probe has a higher Tm than its associated quencher probe. In some embodiments, melting or annealing curves are normalized using background fluorescence at a temperature at which no probe is bound, above 70° C. in FIG. 3, panel A, and the normalized curve can then be plotted directly or can be converted to a first derivative curve which is then plotted. In some embodiments, a background fluorescence curve is obtained using signaling and quencher probes in the absence of target DNA (i.e., no template control), and melting or annealing curves are normalized to the no template curve to correct for background fluorescence throughout the temperature range.

Signaling and quenching probes useful in methods provided herein are typically mismatch tolerant (capable of hybridizing to single-stranded nucleic acid target sequences containing one or more mismatched nucleotides, or deletions or additions). In some embodiments, the presence of mutations is detected by the unique temperature-dependent fluorescence signatures generated by mismatches between probes and target sequences. In some embodiments, probes may be allele-specific (capable of hybridizing only to a perfectly complementary single-stranded nucleic acid target sequence in the method). In some embodiments, one probe of a set may be allele-specific; and the other probe, mismatch tolerant.

Experiments conducted during development of embodiments provided herein demonstrated that secondary structure of a target strand outside the sequences to which probes hybridize can affect the results of annealing or melting analysis. Accordingly, in some embodiments, not every nucleotide in a nucleic acid target sequence needs to be hybridized to a probe. For example, if the target sequence contains a hairpin, the corresponding probe can be designed in some cases to hybridize across the base of the hairpin, excluding the hairpin sequence. In preferred embodiments, both the signaling and quencher probes of a probe set are mismatch tolerant. In some embodiments, a probe set may include an allele-specific signaling probe and an allele-specific quencher probe, a mismatch-tolerant signaling probe and a mismatch-tolerant quencher probe, an allele-specific signaling probe and a mismatch-tolerant quencher probe, or a mismatch-tolerant signaling probe and an allele-specific quencher probe. A mismatch-tolerant probe may be perfectly complementary to one variant of an mtDNA target sequence (e.g. wild-type, a common variant, a selected variant, the Anderson sequence, etc.), or it may be a consensus probe that is not perfectly complementary to any mtDNA variant. Multiple probe sets may include combinations of sets of any of the foregoing types. Additionally, analytical methods provided herein may utilize one or more signaling/quenching probe sets in combination with one or more conventional probes that signal upon hybridization to their target, for example, molecular beacon probes.

In some embodiments, unlabeled oligonucleotides are configured to bind to regions at or near the target sequences for primers, signaling probes, or quencher probes. In some embodiments, these silent probes disrupt secondary structure within or near the target sequences and assist other probes in binding to target sequences at suitable, desired, or optimal Tm for subsequent analysis. In some embodiments, unlabeled oligonucleotides which serve as "openers" of structural elements (e.g. secondary structural elements) are provided.

Probes useful in the methods provided herein may be DNA, RNA, or a combination of DNA and RNA. They may include non-natural nucleotides, for example, PNA, LNA, or 2' o-methyl ribonucleotides. They may include non-natural internucleotide linkages, for example, phosphorothioate linkages. The length of a particular probe depends upon its desired melting temperature (Tm), whether it is to be allele-specific or mismatch tolerant, and its composition, for example, the GC content of a DNA probe.

In some embodiments, each signaling probe has a separate quenching probe associated with it. In some embodiments, one probe (e.g. quencher or signaling probe) may be a part of two probe sets. For example, a quencher probe may be labeled with a quencher at each end, whereby the ends interact with different signaling probes, in which case three probes comprise two probe sets. Also, some embodiments may utilize both ends of a quenched signaling probe, for example, a molecular beacon signaling probe having a fluorophore on one end and a quencher on the other end. The fluorophore on the signaling probe interacts with a quencher on the adjacent quencher probe, thereby comprising one set of probes, while the quencher on said signaling probe interacts with a fluorophore of an adjacent signaling probe, thereby comprising a second set of probes.

For analysis of multiple targets within mtDNA (e.g. HV2, CO2, ND1, etc.), the probe sets that are used are detectably distinguishable, for example by emission wavelength (color) or melting temperature (Tm). Making a probe set distinguishable by Tm from other probe sets is accomplished in any suitable way. For example, in some embodiments, all signaling probes in an assay have different Tm's. Alternatively, in some embodiments, all signaling probes have the same Tm, but the quencher probes have different Tm's. In some embodiments, probe sets are distinguishable by a combination of the signaling probe Tm and quenching probe Tm. Fluorescence detectors can commonly resolve 1-10 differently colored fluorophores. Therefore assays utilizing method provided herein can make use of up to 10 fluorophores (e.g. 1, 2, 3, 4, 5, 6, 7, 8, 9, 10, or more if fluorescence detectors allow). The same fluorescence emitter, for example, the same fluorophore, can be used on more than one signaling probe for a sample, if the signaling probe's can be differentiated for detection by their melting temperatures. In assays provided herein, Tm's could be separated by 0° C. In some embodiments, Tm's are separated by at least 2° C., at least 5° C., and in certain embodiments by at least 10° C. Available temperature space constrains the use of multiple signaling probes having the same fluorophore. If an assay is designed for annealing and/or melt analysis over a range of 80° C. to 20° C., for example, one can utilize more probe sets sharing a color than one can use in an assay designed for such analysis over a range of 70° C. to 40° C., for which one may be able to use only 3-5 probe sets sharing a color. Using four colors and only two probe sets sharing each color, a four-color detector becomes equivalent to an eight-color detector used with eight probes distinguishable by color only. Use of three probe sets sharing each of four colors, twelve different probes sets become distinguishable.

In some embodiments, it is preferred that quencher probes have lower Tm's than their associated signaling probes. With that relationship, the signaling probe emits a temperature-dependent signal through the annealing temperature range of both probes of the set as the temperature of the solution is lowered for an annealing curve analysis, and through the melting temperature range of both probes of the set as the temperature of the solution is raised for a melting curve analysis. If, on the other hand, the quencher probe of a probe set has a higher Tm than its associated signaling probe, the signaling probe's emission is quenched through the annealing temperature range and melting temperature range of both probes of the set, and no fluorescent signal is emitted for detection. This can be ascertained by examination of the annealing curve or the melting curve. The below-background signal also provides useful information about the temperature dependent melting/annealing properties of both the signaling probe and the quenching probe.

Melting temperature (Tm) means the temperature at which a nucleic acid hybrid, for example, a probe-target hybrid or primer-target hybrid, is 50% double-stranded and 50% single-stranded. For a particular assay the relevant Tm's may be measured. Tm's may also be calculated utilizing known techniques. In some embodiments, preferred techniques are based on the "nearest neighbor" method (Santa Lucia, J. (1998), PNAS (USA) 95: 1460-1465; and Allawi, H. T. and Santa Lucia, J. (1997), Biochem. 36: 10581-10594). Computer programs utilizing the "nearest neighbor" formula are available for use in calculating probe and primer Tm's against perfectly complementary target sequences and against mismatched target sequences. In this application the Tm of a primer or probe is sometimes given with respect to an identified sequence to which it hybridizes. However, if such a sequence is not given, for mismatch-tolerant probes that are perfectly complementary to one variant of a single-stranded nucleic acid target sequence, the Tm is the Tm against the perfectly complementary variant. In many embodiments there will be a target sequence that is perfectly complementary to the probe. However, methods may utilize one or more mismatch-tolerant primers or probes that are "consensus primers" or "consensus probes." A consensus primer or probe is a primer or probe that is not complementary to any variant target sequence or, if not all possible target sequences are, to any expected or known sequence. A consensus primer is useful to prime multiple variants of a target sequence at a chosen amplification annealing temperature. A consensus probe is useful to shrink the temperature space needed for analysis of multiple variants. For a consensus primer or probe, if no corresponding target sequence is given, the Tm refers to the highest Tm against known variants, which allows for the possibility that an unknown variant may be more complementary to the primer or probe and, thus, have higher primer-target Tm or probe-target Tm.

In some embodiments, assays provided herein may utilize probe concentrations that are greater than or less than target nucleic acid concentration. The probe concentrations are known on the basis of information provided by the probe manufacturer. In the case of target sequences that are not amplified, target concentrations are known on the basis of direct or indirect counting of the number of cells, nuclei, chromosomes, or molecules are known to be present in the sample, as well as by knowing the expected number of targets sequences usually present per cell, nucleus, chromosome, or molecule. In the case of target sequences that are amplified, there are a number of ways to establish how many copies of a target sequence have been generated over the course of an amplification reaction. For example, in the case of a LATE-PCR amplification reaction the number of single-stranded amplicons can be calculated as follows: using a signaling probe without a quencher (in the case of quenched signaling probe that means the probe minus the quencher) in a limiting concentration such as 50 nM and its corresponding quencher probe in excess amount such as 150 nM, the number of cycles it takes to decrease the fluorescence to zero (or, in practical terms, to its minimal background level) is proportional to the rate of amplification of single-stranded amplicons. When fluorescence reaches zero (minimal background level), all of the signaling probes have found their target, and the concentration of the amplicons exceeds that of the signaling probe. In certain embodiments an amplification reaction may be continued until the amplicon being produced reaches a "terminal concentration." Experiments conducted during development of embodiments provided herein demonstrated that a LATE-PCR amplification begun with differing amounts of target tends to eventually produce the same maximum concentration of amplicon (the "terminal concentration"), even though amplification begun with a high starting amount of target reaches that maximum in fewer cycles than does the amplification begun with a low starting amount of target. To achieve the terminal concentration beginning with a low amount of target may require extending the amplification through 70 or even 80 cycles.

Some embodiments utilize probe sets in which the concentration of the signaling probe is lower than the concentration of its associated quencher probe. This ensures that, when both probes are hybridized to their at least one nuclei acid target sequence, the signaling probe is quenched to the greatest possible degree, thereby minimizing background fluorescence. It will be appreciated that background fluorescence in an assay is the cumulated background of each signaling probe of a given color and that probes of a different color may contribute further to background signal.

Methods provided herein include analyzing the hybridization of probe sets to single-stranded mtDNA target sequences. In methods provided herein, hybridization of signaling probes and quencher probes as a function of temperature are analyzed for the purpose of detecting or otherwise analyzing mutations and/or mutational load in an mtDNA target sequence in a sample. In some embodiments analysis includes obtaining a curve or, if multiple colors are used, curves of signals from signaling probes as the temperature of a sample is lowered (see FIG. 3, Panel F) or obtaining a curve or curves of signals as the sample temperature is raised, or both. It is known that the shapes of the two types of curves are not necessarily identical due to secondary structures. Either or both of those curves can be compared to a previously established curve or a curve from a control sample for a known single-stranded nucleic acid target sequence as part of the analysis, for example, detecting mutations in the mtDNA target sequence. In some embodiments, analysis comprises quantitating the mutational load in the single-stranded mtDNA target sequence being probed. Derivative curves can also be utilized to obtain, for example, the Tm of a signaling probe against a nucleic acid target sequence. It is not always necessary, and it may not be desirable, to utilize entire fluorescence curves or their derivatives. In certain embodiments analysis of the hybridization of signaling probes and quencher probes includes obtaining fluorescence readings at one or several temperatures as the sample temperature is lowered or raised, where those readings reflect an effect on each signaling probe due to its associated quencher probe. In most embodiments analysis will include signal increase, signal decrease, or both, from signaling probes.

In some embodiments, fluorescence readings using a particular probe set over a range of temperatures generates a temperature-dependent fluorescence signature. A temperature-dependent fluorescence signature may comprise curves, data points, peaks, or other means of displaying and/or analyzing an assay or sample. In some embodiments, analysis of temperature-dependent fluorescence signatures detects mutations in mtDNA. In some embodiments, analysis of temperature-dependent fluorescence signatures locates and/or identifies mutations in mtDNA. In some embodiments, analysis of temperature-dependent fluorescence signatures measures the mutational load in mtDNA. In some embodiments, analysis is performed by a user. In some embodiments, analysis is performed by analysis software on a computer or other device.

In some embodiments, methods provided herein include nucleic acid amplification. Some preferred methods are those which generate the target sequence or sequences in single-stranded form. LATE-PCR amplification of DNA sequences or RNA sequences (RT-LATE-PCR) is especially preferred in some embodiments. LATE-PCR amplifications and amplification assays are described in, for example, European patent EP 1,468,114 and corresponding U.S. Pat. No. 7,198,897; published European patent application EP 1805199 A2; Sanchez et al. (2004) Proc. Nat. Acad. Sci. (USA) 101: 1933-1938; and Pierce et al. (2005) Proc. Natl. Acad. Sci. (USA) 102: 8609-8614. All of these references are hereby incorporated by reference in their entireties. LATE-PCR is a non-symmetric DNA amplification method employing the polymerase chain reaction (PCR) process utilizing one oligonucleotide primer (the "Excess Primer") in at least five-fold excess with respect to the other primer (the "Limiting Primer"), which itself is utilized at low concentration, up to 200 nM, so as to be exhausted in roughly sufficient PCR cycles to produce fluorescently detectable double-stranded amplicon. After the Limiting Primer is exhausted, amplification continues for a desired number of cycles to produce single-stranded product using only the Excess Primer, referred to herein as the Excess Primer strand. LATE-PCR takes into account the concentration-adjusted melting temperature of the Limiting Primer at the start of amplification, $Tm_{[0]}^L$, the concentration-adjusted melting temperature of the Excess Primer at the start of amplification, $Tm_{[0]}^X$, and the melting temperature of the single-stranded amplification product ("amplicon"), $Tm_A$. For LATE-PCR primers, $Tm_{[0]}$ can be determined empirically, as is necessary when non-natural nucleotides are used, or calculated according to the "nearest neighbor" method (Santa Lucia, J. (1998), PNAS (USA) 95: 1460-1465; and Allawi, H. T. and Santa Lucia, J. (1997), Biochem. 36: 10581-10594) using a salt concentration adjustment, which in our amplifications is generally 0.07 M monovalent cation concentration. For LATE-PCR the melting temperature of the amplicon is calculated utilizing the formula: $Tm=81.5+0.41$ (% G+% C)$-500/L+16.6 \log [M]/(1+0.7 [M])$, where L is the length in nucleotides and [M] is the molar concentration of monovalent cations. Melting temperatures of linear, or random-coil, probes can be calculated as for primers. Melting temperatures of structured probes, for example molecular beacon probes, can be determined empirically or can be approximated as the Tm of the portion (the loop or the loop plus a portion of the stem) that hybridizes to the amplicon. In a LATE-PCR amplification reaction $Tm_{[0]}^L$ is preferably not more than 5° C. below $Tm_{[0]}^X$, more preferably at least as high and even more preferably 3-10° C. higher, and $Tm_A$ is preferably not more than 25° C. higher than $Tm_{[0]}^X$, and for some preferred embodiments preferably not more than about 18° C. higher.

LATE-PCR is a non-symmetric PCR amplification that, among other advantages, provides a large "temperature space" in which actions may be taken. See WO 03/054233 and Sanchez et al. (2004), cited above. Certain embodiments of LATE-PCR amplifications include the use of hybridization probes, in this case sets of signaling and quencher probes, whose Tm's are below, more preferably at least 5° C. below, the mean primer annealing temperature during exponential amplification after the first few cycles. Sets of signaling and quencher probes are included in LATE-PCR amplification mixtures prior to the start of amplification. A DNA dye, if used, can also be incorporated into the reaction mixture prior to the start of amplification.

In some embodiments, samples which find use in the methods include clinical samples, diagnostic samples, research samples, forensic samples, environmental samples, etc. are provided. In some embodiments, samples utilize processing (e.g., purification, stabilization, etc.) by one or more techniques understood in the art prior to use in methods described herein.

While the specification focuses on analysis of mtDNA, one of skill in the art will appreciate that the compositions and methods described herein may be employed on other types of nucleic (e.g., genomic DNA), for example, to assess mutations in desired nucleic acid target regions (e.g., gene sequences, non-coding sequences, repeat sequences, etc.). The methods and compositions described herein are useful for finding unanticipated mutations in type of nucleic acid, including, cpDNA, viral nucleic acid, plasmid nucleic acid, bacterial nucleic acid, genomic DNA, etc. In certain embodiments, the target nucleic acid is a methylated stretch of nucleic acid, where, for example, the methylation tends to hide or obscure the presence of the mutations. Known methods, such as bisulphate methods, can be employed to find such methylated mutations.

The present invention is not limited by the species from which the target nucleic acid is isolated or derived. In certain embodiments, the target nucleic acid is from an animal selected from the group consisting of: mice, rat, dog, cat, horse, cow, pig, fish, or other animal. In some embodiments, the target nucleic acid is from a human. In certain embodiments, the target nucleic acid is from CHO cells, or other cultured cells.

In certain embodiments, AT-rich tails, mismatched to target, are present on the 5' end of the limiting primers. In a multiplex assays, single-stranded amplicons accumulate in a single reaction simultaneously, there is an increased probability that the various products can interact, a phenomenon known as product evolution. Product evolution occurs when the 3' end of one product hybridizes to and extends on another product molecule. Since PrimeSafe inhibits the extension of mis-matched 3'-ends of primers, the 5'ends of all the limiting primers in a multiplex may be designed to have non-complementary AT rich tails. These added bases become the 3'ends of the single-stranded amplicons and the fact that they are AT rich decreases the probability that they will hybridize to another product molecule and trigger product evolution. In sum, addition of PrimeSafe (or other reagents that suppress mis-priming) and the use of limiting primers with non-complementary AT rich 5' ends clean up amplification in LATE-PCR multiplex reactions and allowed for clean amplification.

BRIEF DESCRIPTION OF THE DRAWINGS

FIGS. 2A-2C show primers and probes, and their corresponding hybridization sites on the (A) HV2 (SEQ ID NO:7), (B) CO2 (SEQ ID NO:8), and (C) ND1 targets (SEQ ID NO:9). Quencher (Q) and fluorescent (F) labels are indicated at the ends of the probes, and mismatches to the Anderson Sequence are indicated with lowercase.

DESCRIPTION

Figure 1:
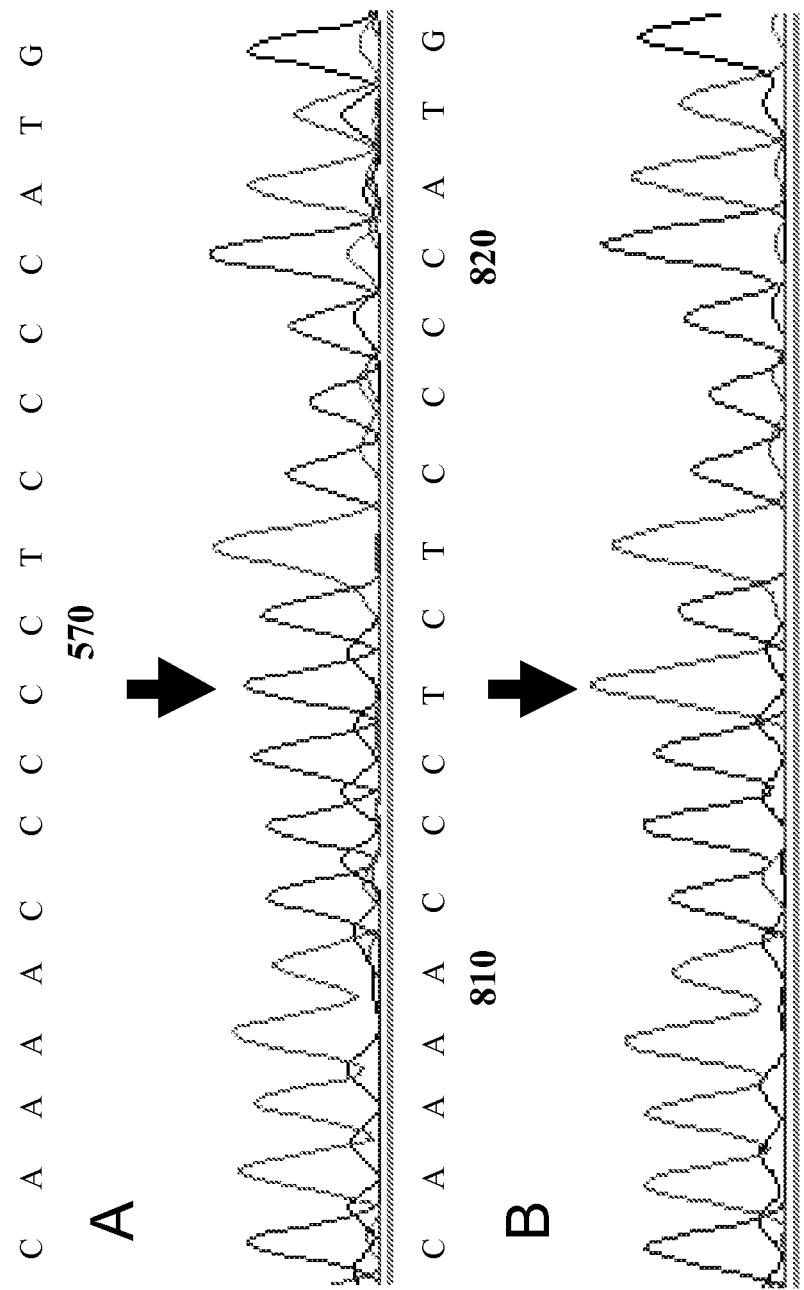
FIG. 1 shows sequence analysis of the HV1 region of a hair sample: (A) the sample at a population level (1000-copies of mtDNA), (B) the same sample as (A), but diluted to a single copy of mtDNA. The mutation is only observed at the single copy level, because the population data is an averaged over the entire sample.

Provided herein are methods for detecting mutations in nucleic acid, and compositions and kits for performing such methods. In particular, nucleic acid amplification and fluorescence detection methods are provided to detect mutations and assess the mutational load. In some embodiments, compositions, kits, and methods are provided to detect mutations and assess mutational load in nucleic acids, including, but not limited to: RNA, cDNA, genomic DNA, and non-genomic DNA. In some embodiments, mutations and mutational load are assessed in non-genomic DNA including, but not limited to: mitochondrial DNA, chloroplastic DNA, episomal DNA, etc. Embodiments described herein focus on detection of mutations and assessment of mutational load in mitochondrial DNA (mtDNA); these embodiments should be viewed as illustrative, as the methods provided are also applicable to other nucleic acids (e.g. genomic DNA, chloroplastic DNA, etc.).

Mutations in mtDNA have been linked with human diseases including diabetes, cancer, Parkinson's, and Alzheimer's. There is little evidence that specific point mutations cause the onset of these diseases. It is believed that the generation of random mutations throughout the mtDNA, over time, lead to mitochondrial dysfunction and disease. The buildup of random mutations results in an increased mutational load, signaling and/or causing disease onset. It is because these mutations happen rarely, but accumulate over time, together with the fact that each eukaryotic cell has a great many mitochondrial genomes, that it is very difficult to identify mutation X as the cause of disease Y.

Amplification and analysis of bulk samples prepared from large numbers of mtDNA molecules is generally only useful for detecting the most abundant mutations—which may or may not play a significant role in disease development under mutational load conditions. In order to observe the increase in mutations over time, it is necessary to amplify very few, typically <10 or even single mtDNA molecules. One solution to this problem is to sequence individual molecules of DNA, known as digital sequencing, but this approach is both time consuming and expensive. An alternative approach involves the use of "deep" sequencing methods, but this approach is also expensive (He et al. (2010) Nature 464, 610-614.; herein incorporated by reference in its entirety).

This effect is highlighted in the case of Alzheimer's Disease (AD). There is strong evidence that AD is associated with mitochondrial dysfunction. Much study has been conducted to see if mtDNA mutations are linked to the onset of disease. However, in the case of AD no two "associated" mutations have ever been reproduced between research groups (Onyango. (2006) Journal of Alzheimer's Disease 9, 183-193.). The lack of reproducibility may be due to the population based approach of these studies.

Recent studies have demonstrated that while Nucleoside Reverse Transcriptase Inhibitors (NRTIs) have been hugely successful in treatment of HIV/AIDs, they may in fact be causing a whole new set of diseases, such as cancer, heart disease, and Parkinson's Disease (Fleischman et al. (2007) American Journal of Physiology-Endocrinology and Metabolism 292, 1666-1673.; herein incorporated by reference in its entirety). NRTIs used to treat HIV/AIDS, have recently been shown to damage mitochondria and cause dysfunction (Martin et al (2003) American Journal of Human Genetics 72, 549-560.; Cote et al. (2002) New England Journal of Medicine 346, 811-820.; herein incorporated by reference in their entireties). There is a need for tracking random low levels of mutations (mutational load) caused by drugs and/or disease to see if such damage results in dysfunction and disease. In order to study these low frequency events, one cannot look at large populations of mtDNA, but must focus on single molecules of mtDNA to observe the buildup of mutations over time. NRTI's are sometimes combined and used in mixtures, but the impact of such mixtures on mtDNA integrity is little known. In addition, NRTI's are just one class of drugs and chemicals known to damage mtDNA and little is known about the effects of these chemicals and pharmaceuticals on the integrity of mtDNA, whether such chemical and pharmaceuticals are used alone or in combination, and whether they are deliberately prescribed by a physician for short term or long term use, or these drugs and or chemicals are inadvertently experienced by a person.

In this regard particular attention needs to be paid to mtDNA integrity in many types of fetal cells, and many types of cells in newborn infants, including all types of stem cells, and most particularly including primordial germ cells of a female fetus or a newborn female infant, because these cells are the source of all mitochondrial genomes inherited through the maternal lineage. Moreover, in light of advances in the fields on in vitro fertilization and stem cells, particular attention needs to be paid in these regards to the effects of chemicals, biochemicals, drugs and other agents used to deliberately in vitro treat or inadvertently expose cells, including germ cells, embryonic cells, stem cells, and all other types of agents which damage or alter mtDNA molecules.

Provided herein are methods for detecting mutations in mitochondrial DNA (mtDNA), and compositions and kits for performing such methods. In particular, nucleic acid amplification and fluorescence detection methods are provided to detect mutations and assess the mutational load of mtDNA. In some embodiments, methods, kits, and compositions herein provide assays capable of detecting and identifying random unique mutations in target sequences (e.g. mtDNA target sequences). In some embodiments, the methods herein do not depend upon prior knowledge of the location of a mutation within the target region. In some embodiments, the methods herein do not depend upon prior knowledge of the number of mutations within the target region. In some embodiments, methods herein detect the buildup of mutational load in target nucleic acids (e.g. mtDNA). In some embodiments, increase in mutational load is the result or side effect of age, environmental hazards, genetic susceptibility, diet, pharmaceuticals (e.g. Nucleoside Reverse Transcriptase Inhibitors, AZT, etc.), or a combination of causes. In some embodiments, methods herein track mutational load in target nucleic acid (e.g. mtDNA) that is associated with the onset of disease states. In some embodiments, methods herein track mutational load in target mtDNA that is associated with the onset of diseases (e.g. mitochondrial disease), such as diabetes or Parkinson's disease. In some embodiments, methods provided herein are applicable to detection of mutations and assessment of mutational load in any gene or target nucleic acid, whether it is located within mtDNA, nuclear DNA, RNA, etc.

In some embodiments, provided herein are methods, kits, and compositions configured to amplify and probe, in a single tube genes or regions of nucleic acid to detect or identify mutations, or assess or quantify mutational load. In some embodiments, target nucleic acids are within mtDNA or nuclear DNA. In some embodiments, quencher and signaling probe sets are configured to hybridize to target nucleic acids (e.g. targets within mtDNA). In some embodiments, multiple probe sets (quencher and signaling probes) are used to probe a target. In some embodiments, multiple targets are probed.

In some embodiments, methods, kits, and compositions provided herein are configured to amplify and probe, in a single tube, three genes or regions of the mitochondrial genome (e.g. human mitochondrial genome): cytochrome c oxidase subunit 2 (CO2), NADH dehydrogenase, subunit 1 (ND1), and the hyper variable 2 (HV2) of the D-Loop. Each of these regions has sequence changes (mutations) that are related to disease (e.g. human disease). It has also been demonstrated that these regions develop mutations in response to low level AZT exposure. In some embodiments, primer pairs (e.g., SEQ ID NOs:1-6) generate mtDNA target amplicons of 586 base pairs (CO2), 604 base pairs (ND1) and 588 base pairs (HV2) in length. In some embodiments, each target sequence is probed using 10 (HV2 and ND1) or 12 (CO2) separate probes. Collectively, probes span 250 or 300 base pairs of their respective target sequences. In some embodiments, 5 signaling probes (HV2 and ND1) and/or 6 signaling probes (CO2) are provided. In some embodiments, signaling probes are molecular beacon probes with two-nucleotide-long stems. In some embodiments, each of the probe sets (HV2, ND1, and CO2) are labeled with a quencher on one end (e.g. Black Hole Quencher 2), and a fluorescent label on the other. In some embodiments, each probe set (HV2, ND1, and CO2) is labeled with a fluorescent label that is distinct from the others. In some embodiments, the HV2 probes have Quasar 670 on one end and a Black Hole Quencher 2 on the other end. In some embodiments, the CO2 probes have Cal Red 590 on one end and a Black Hole Quencher 2 on the other end. In some embodiments, the ND1 probes have Cal Orange 560 on one end and a Black Hole Quencher 1 on the other end. In some embodiments, other combinations of fluorescent labels and probe sets are utilized. In some embodiments, 5 quencher probes (HV2 and ND1) and/or 6 quencher probes (CO2) are provided. In some embodiments, quencher probes are terminally labeled with a quencher (e.g. Black Hole Quencher).

Provided herein are compositions (e.g., reagents, reactions mixtures, etc.), methods (e.g., research, screening, diagnostic), and systems (e.g., kits, data collection and analysis) for detection of mutations in mtDNA. In particular, provided herein are compositions, methods, and systems that permit detection of mutations (e.g. random mutations) in mtDNA. In some embodiments, multiplex, single-tube reactions are provided that can detect mutations in a mixed sample, and determine the mutational load for the mtDNA of a subject.

For example, provided herein is a set of single-tube homogeneous multiplexed assays for detection of mutations in mtDNA. In some embodiments, assays provided herein utilize LATE-PCR (U.S. Pat. No. 7,198,897; incorporated herein by reference in its entirety), PRIMESAFE II (PRIMESAFE is a trademark of Smiths Detection Inc.)(U.S. Patent Application No. 20080193934; incorporated herein by reference in its entirety), and Lights-On/Lights-Off probe sets (International Application No. PCT/US10/53569; incorporated herein by reference in its entirety).

Compositions, kits, and methods provided herein provide sensitive and robust amplification starting with low initial numbers of target sequences (e.g. either absolute numbers or relative to non-target sequences). In some embodiments, amplified target sequences which are substantially longer than individual fluorescent hybridization probes are analyzed using sets of probes which use the same colored fluorophore.

In some embodiments, signaling probes and quenching probes for use with mtDNA mutation detection assays are provided. Signaling probes and quenching probes are typically mismatch tolerant. A mismatch-tolerant probe hybridizes in the assay, not only to a target sequence that is perfectly complementary to the probe, but also to variations of the target sequence that contain one or more mismatches due to substitutions, additions or deletions. For mismatch-tolerant probes, the greater the variation of the target from perfect complementarity, the lower the Tm of the probe-target hybrid. In some embodiments, sequence-specific probes are employed. A sequence-specific probe hybridizes in the assay only to a target sequence that is perfectly complementary to the probe (e.g. at a given temperature). In some embodiments, combinations of sequence-specific and mismatch-tolerant probes are employed in an assay. If a probe is sequence-specific, its lack of hybridization will be apparent in the melt curve and the derivative curve. For example, if a signaling probe hybridizes, causing an increase in fluorescence, but its associated quencher probe does not hybridize, fluorescence will not decrease as the temperature is lowered through the Tm of the quencher probe, revealing that the quencher probe did not hybridize and indicating a target mutation in the sequence complementary to the quencher probe. While this result indicates a mutation in the target sequence for the quencher probe, it does not allow for determination of which mutation is present, or how many mutations are present. In some embodiments, it is preferable that the associated quencher probe be mismatch tolerant. In some embodiments, mismatch tolerant probes allow determination of the identity, location, and/or number of mutations in an mtDNA target sequence, cpDNA target sequence, or any other target sequence where it is useful to find unanticipated mutations. In some embodiments, mismatch tolerant probes allow assessment of the mutational load in an mtDNA or other target sequences. In some embodiments, mismatch tolerant probes provide for differentiation of different mutations, distinguished by their different effects on the melting curve (and derivative curve) due to differing Tm effects of different mutations.

In some embodiments, a signaling probe of a set has a higher Tm with respect to the single-stranded nucleic acid target sequence than does its associated quencher probe. With that relationship, as a sample is subjected to melt analysis, for example, as temperature is increased signal first increases as the quencher probe melts off and then decreases as the signaling probe melts off. With the opposite relationship, signal remains quenched as the lower Tm signaling probe melts off and does not then increase as the higher Tm quencher probe melts off. The preferred relationship thus provides more information. In some embodiments, it is preferred that the quencher probe of a set reduces the signal from its associated signaling probe to a very large extent. In such embodiments, it is preferred that the concentration of the quencher probe equal or exceed the concentration of the signaling probe. In order to maximize signal amplitude, certain embodiments utilize probe concentrations that are in excess with respect to the single-stranded nucleic acid target sequence, thereby ensuring that all or nearly all copies of the target sequence will have hybridized probes.

Methods provided herein include the use of a single set of interacting signaling and quencher probes. Methods also include the use multiple sets of interacting signaling and quencher probes, wherein each signaling probe is detectably distinguishable from the others. Distinction of fluorescent probes may be by color (emission wavelength), by Tm, or by a combination of color and Tm. Multiple sets of interacting probes may be used to interrogate a single target sequence or multiple target sequences in a sample, including multiple target sequences on the same target strand or multiple target sequences on different strands. Multiplex detection of multiple target sequences may utilize, for example, one or more sets of signaling/quencher probes specific to each target sequence. In some embodiments, multiplex methods utilize a different fluorescent color for each target sequence. Certain embodiments utilize the same color for two different target sequences, available temperature space permitting.

Figure 3:
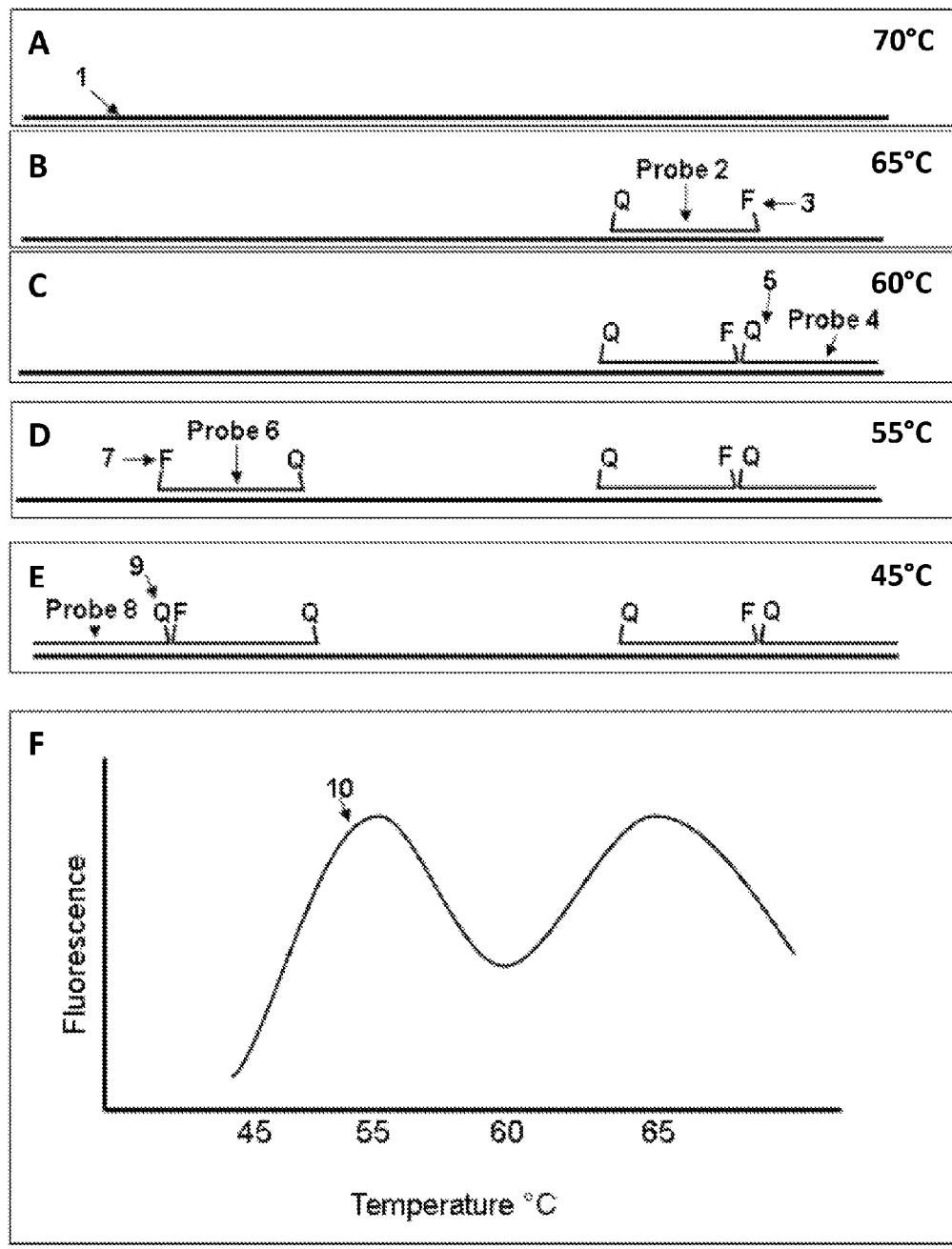
FIG. 3 shows an exemplary probing assay provided herein: A-E are schematics showing hybridization of two sets of signaling and quencher probes to a single-stranded nucleic acid target sequence in a sample as a function of temperature; F shows the fluorescence versus temperature of the sample in the presence and absence of a target sequence.

In some embodiments, methods comprise analyzing hybridization of signaling/quencher probe sets to one or more single-stranded mtDNA target sequences as a function of temperature. Signal, preferably fluorescent signal, from the signaling probe or probes may be acquired as the temperature of a sample is decreased (annealing) or increased (melting). Analysis may include acquisition of a complete annealing or melting curve, including both increasing and decreasing signals from each signaling probe, as is illustrated in FIG. 3, Panel F. In some embodiments, an annealing or melting curve is normalized against background fluorescence by comparing it to a curve obtained using the same probe sets in the absence of a target sequence (i.e. no template control). In some embodiments, an annealing or melting curve is normalized against background fluorescence by subtracting no template control curve. Alternatively, analysis can be based only on signal increase or signal decrease. Analysis may utilize only signals at select temperatures rather than at all temperatures pertinent to annealing or melting.

In methods provided herein, one or more single-stranded mtDNA or cpDNA or other target sequences to be analyzed may be provided by nucleic acid amplification, generally exponential amplification. In some embodiments, the amplification is a digital amplification method (e.g., digital PCR). In some embodiments, the amplification does not employ a digital amplification process. Any suitable nucleic amplification method may be used. Preferred amplification methods are those that generate amplified product (amplicon) in single-stranded form so that removal of complementary strands from the single-stranded target sequences to be analyzed is not required. Probe sets may be included in such amplification reaction mixtures prior to the start of amplification so that reaction vessels containing amplified product need not be opened. When amplification proceeds in the presence of probe sets, it is preferred that the system be designed such that the probes do not interfere with amplification. In some embodiments a non-symmetric PCR method such as asymmetric PCR or, LATE-PCR is utilized to generate single-stranded copies. PCR amplification may be combined with reverse transcription to generate amplicons from RNA targets. For example, reverse transcription may be combined with LATE-PCR to generate DNA amplicons corresponding to RNA targets or the complements of RNA targets. In some embodiments, amplification methods that generate only double-stranded amplicons are not preferred, because isolation of target sequences in single-stranded form is required, and melt-curve analysis is more difficult with double-stranded amplicons due to the tendency of the two amplicons to collapse and eject hybridization probes. In some embodiments, methods provided herein do not utilize generation of detectable signal by digestion of signaling probes, such as occurs in 5' nuclease amplification assays. In a PCR amplification reaction, for example, avoidance of probe digestion may be accomplished either by using probes whose Tm's are below the primer-extension temperature, by using probes such as those comprising 2' O-methyl ribonucleotides that resist degradation by DNA polymerases, or by using DNA polymerases that lack 5' exonuclease activity. Avoidance of probe interference with amplification reactions is accomplished by utilizing probes whose Tm's are below the primer-extension temperature such that the probes are melted off their complementary sequences during primer extension and, most preferably, during primer annealing, at least primer annealing after the first few cycles of amplification.

In LATE-PCR amplification, for example, the Excess Primer strand is the single-stranded amplicon to which probe sets hybridize. It therefore is or contains the single-stranded nucleic acid sequence that is analyzed. Its 5' end is the Excess Primer, and its 3' end is the complement of the Limiting Primer. If the sequence to be analyzed lies between the Excess Primer and the Limiting Primer, the starting sequence that is amplified and the Excess Primer strand both contain that sequence. If in the starting sequence to be amplified the sequence desired to be analyzed includes a portion of either priming region, it is required that the primer be perfectly complementary to that portion so that the Excess Primer strand contain the desired sequence. Primers need not be perfectly complementary to other portions of the priming regions. Certain embodiments of methods provide single-stranded nucleic acid target sequence to be analyzed by amplification reactions that utilize "consensus primers" that are not perfectly complementary to the starting sequence to be amplified, and care is taken to ensure that the Excess Primer strand, which is or contains the single-stranded target sequence that is actually analyzed, contains the desired sequence.

In some embodiments, assays provided herein utilize PRIMESAFE II (described in U.S. Patent Application No. 20080193934; herein incorporated by reference in its entirety). PRIMESAFE II is a class of reagents added to PCR reactions to suppress mis-priming. PRIMESAFE II reagents are comprised of linear oligonucleotides that are chemically modified at their 5' and or 3' ends. In some embodiments, the assays described here make use of a formulation of PRIMESAFE II that has three strands, the first two strands of which are modified at both the 5'end and the 3'end by covalent linkage of dabcyl moieties, the third strand of which is complementary to said first two strands dependent on the temperature of the reaction dependent on the temperature of the reaction and is chemically modified by addition of dabcyl moieties at both the 5'end and the 3'end. In some embodiments, the assays described herein make use of other reagents added to the reaction to suppress mis-priming (and/or improve specificity). In particular embodiments, particular nucleic acid sequences are used to suppress mis-priming.

In addition to detecting mutations and assessing mutational load to detect diseases or risk for disease onset, the compositions and methods described herein find utility in a variety of clinical, diagnostic, therapeutic, and research applications. In some embodiments, methods provided herein detect mutations and assess mutational load in any class or type of cells, e.g., to assess DNA damage. In some embodiment, mutational load is assessed in transplant cells, stem cells (e.g. hematopoietic, fetal, adult, embryonic), bone marrow, etc., e.g., to determine the extent of DNA damage present. The methods described herein are not limited as to their field of application.

EXPERIMENTAL

Features and embodiments of methods provided herein are illustrated in the Examples set forth below in conjunction with the accompanying Figures. The Examples should be viewed as exemplary and not limiting in scope.

Example 1

Compositions and Methods

Experiments were conducted during development of embodiments provided herein to demonstrate the capabilities of the methods to analyze sequence changes in the mitochondrial genome caused by mutagens, drugs, environmental chemicals and conditions, aging, and additional unknown causes. A LATE-PCR amplification was performed using three pairs of primers to amplify three genes or regions of the mitochondrial genome: cytochrome c oxidase subunit 2 (CO2), NADH dehydrogenase, subunit 1 (ND1), and the hyper variable 2 (HV2) of the D-Loop. All of these regions have sequence changes that are related to human disease. The triplex amplification provided amplicons of 586 base pairs (CO2), 604 base pairs (ND1) and 588 base pairs (HV2). Following amplification, each single-stranded nucleic acid target sequence was probed using 10 (HV2 and ND1) or 12 (CO2) separate probes which were included in the original amplification reaction mixture.

The probes in combination spanned 250, 300, and 250 base pairs of their respective single-stranded target sequences. Five of the probes for HV2 and ND1, and six of the probes for CO2 were signaling probes. All the signaling probes were quenched molecular beacon probes with two-nucleotide-long stems. Each of the HV2 probes included covalently bound labels: the fluorophore Quasar 670 on one end and a Black Hole Quencher 2, BHQ2, (Biosearch Technologies, Novato Calif.), on the other end. Each of the CO2 probes included covalently bound labels: the fluorophore Cal Red 590 on one end and a Black Hole Quencher 2, BHQ2, (Biosearch Technologies, Novato Calif.), on the other end. Each of the ND1 probes included covalently bound labels: the fluorophore Cal Orange 560 on one end and a Black Hole Quencher 1, BHQ1, (Biosearch Technologies, Novato Calif.), on the other end. The other 5 (HV2 and ND1) or 6 (CO2) probes were quencher probes terminally labeled with BHQ2 only. In this example, the Tm's of the signaling probes with respect to the mitochondrial reference sequence (the Anderson Sequence) differed from one another, and the Tm's of the quencher probes with respect to the mitochondrial reference sequence differed from one another.

Reaction components and conditions were as follows. It is noted that the underlined bases in the limiting primers are the bases that are mismatched to their targets, and allow for cleaner amplification by avoiding problems associated with produce evolution as described further above.

```
HV2 Primers
Limiting Primer:
                                                 (SEQ ID NO: 1)
5'-AAAGCGGTGTGTGTGTGCTGGGTAGGAT Excess Primer:
                                                 (SEQ ID NO: 2)
5'-ACTTCAGGGTCATAAAGCCTAAATAGC CO2 Primers
Limiting Primer:
                                                 (SEQ ID NO: 3)
5'-AATAGAGGGGGTAGAGGGGGTGCTATAGGGT Excess Primer:
                                                 (SEQ ID NO: 4)
5'-TCCTTATCTGCTTCCTAGTCCTGTATGC ND1 Primers
Limiting Primer:
                                                 (SEQ ID NO: 5)
5'- AACATAAGAACAGGGAGGTTAGAAGTAGGGTCTTGGT Excess Primer:
                                                 (SEQ ID NO: 6)
5'- CGCCCCGACCTTAGCTCT
```

-continued

Target: HV2

(SEQ ID NO: 7)
5'GCTCGCCACACACACACGACCCATCCTACCCGCCCCCAACATAACTACTCTAATCATC

ATACCCTCACCCTCCCCTTTTATTACACAATCAACCCCCCACTGACAATTTTCACGTATG

GCGGTTTTCTATTTTAAACTTTAGACCAATCCGACCACAATCCCAAGAAACAAAAACCC

CAAACCGTCTCTACACAAATTCACGACACCGGTCTTCGCCCCCTCCCCCCCAAACCACCT

TTAAAAAACAATACTACAGACACACCTTTCACCGACACGTCTGTAAGTTAACAATAATA

ATACAGGATGTTCGTAATTAATTAATTGTGTGAAATCATTCATACAAGCGGACATTATA

ACTTGCATCCACGCTATTTATTATCCTACTCCGTCCTTAGTTTCTGTCTATGACGCTGTAT

CCCACGAGGCCGAGGTCGCAGAGCGTTACGATAGCGCACGTATGGGGGGTCTGCTTTTA

TGGTTTACGTACCTCTCGAGGGCACTCACCAATTATCCCACTATCTGGACACTAGGTAGC

ACTACAGAATAAATTCCCCTTGCACACCCGATAAATCCGAAATACTGGGACTTCA

Target: CO2

(SEQ ID NO: 8)
5'CCCGAGATCTCCCCCATCTCCCCCACGATATCCCATTTATGCCCGGGATAAAGTTTCTA

AAAATCCCCTTAATTAAGATCCTGCTACCCGTACTTTGACACCAAACGAGGTGTCTAAA

GTCTCGTAACTGGCATCATATGGGGGCCAGCACATCGCCACTTTCACCAAACCAAATCT

GCAGGCCCTTAACGTAGACAAAAATTCGGATTACACCCCTGTCGAGTACTCACGTTCTG

CAGAACACTACATTAATAATATGCTTACCCCCGAAGTTAGCCCTCATGATGAGCTAACA

GTTGCAGTTCCTCAGCGTCCAGCGGACCAAGATCCTTATTACCCCCTTCATACATCCTCA

ACTTCTAATCAGGCGGCATCAGCCACATGAGCATCCAAGTCATGGTAACCACCGGTTAA

CTAAACTACCATTCCCTCCCTAGCAACTGGAGCAGACAATACATTTCCTACGCATCCCTA

CCCTCCCGCTACTCCTGATCCTACTACCGCCCGTCCTATCAAGTCTGCCAAAGATAAAGG

ACTCGCAGACTCTACAATCATAATCAATCAAAACAACACTCACAATCCTTTTCCCGTATG

TCCTGATCCTTCGTCTATTCCT

Target: ND1

(SEQ ID NO: 9)
5'AAGTATTCTTGTCCCTCCAATCTTCATCCCAGAACCACTGTTTTATACAACACATCTCA

AGTCCCCTCTCACGCAGTATACAACAAGGATCCTTCTAACATCACCACTCCCACAAATA

ATATTATTACAAACACATAAGCCGATACTTCTTATCCCGCTTCCCCGGACGCCGCATAAG

CTACAACTTCGGACTCTGATCAAGCCTGAGGGGAAGCCGTTCCAGCTTCCCCCAAGCCA

ACCAGAGACGATCACACCTCTATTTAGTATAATACCGGTTCCCAGTACTACCGTCCTCAT

TAGTCTCCACAAGAACACAACACTATTCCCACCTCTCCAATTTCCTCGGTGAATAATCAT

TACAACTATCATCTTACTACCGATCCCACTGAAGTATACTCTAACAAACCCGATGACGA

GCGTCACGCGGCTAGTCCCGCATCAAACTCAAACTACGAGTGGGACTAGTCTCCTAACT

CATTTGCCGATCCGATCTCCACCGATCTTATTTATCCTCCGGATCCAACTCCAACTGGTC

CCCCAACCCATACCCCTCCCCCCAAGTATCATCTTCTCGCTACCACTCTCGATTCCAGCC

CCGC

HV2 Probes
On 1:

(SEQ ID NO: 10)
5'-Quasar 670-TGGTTAGGGTTCTTT<u>A</u>TTTTGGGGTTCA-BHQ2

Off 1:

(SEQ ID NO: 11)
5'-AAT<u>G</u>TGAAAT<u>C</u>TGCTT<u>G</u>GGCTGGT-BHQ2

-continued

On 2:
(SEQ ID NO: 12)
5'-BHQ2-AATGGCAGAGATGTCTTTAAGTGCTGTTT-Quasar 670

Off 2:
(SEQ ID NO: 13)
5'-BHQ2-GGCTAGGAGTTGGGGAGGGCGGGTT-C$_3$

On 3:
(SEQ ID NO: 14)
5'-BHQ2-AAATGTAATCGCGTTCATATCACCCAGTT-Quasar 670

Off 3:
(SEQ ID NO: 15)
5'-BHQ2-ACGAGAGTACCCAACGCATGGAGAG-C$_3$

On 4:
(SEQ ID NO: 16)
5'-Quasar 670-TAATTGAACATAGGTACGATAAATAATTA-BHQ2

Off 4:
(SEQ ID NO: 17)
5'-TTTAGTAAATGTGTTCACCTGTAAT-BHQ2

On 5:
(SEQ ID NO: 18)
5'-Quasar 670-AACTGGGTGAAAAGTGACTATGCGGACTT-BHQ2

Off 5:
(SEQ ID NO: 19)
5'-TGGGGGAAGTTTTTTCTTATTATGT-BHQ2

CO2 Probes
On 1:
(SEQ ID NO: 20)
5'-BHQ2-AAACTACTCGATTATCAACGTCAAGGATT-Cal Red 590

Off 1:
(SEQ ID NO: 21)
5'-BHQ2-GTCGCAGGACGCCTAGTTTTAGGAA-C$_3$

On 2:
(SEQ ID NO: 22)
5'-BHQ2-AAAATGGGGAAGTTTGTATGAGTTGATT-Cal Red 590

Off 2:
(SEQ ID NO: 23)
5'-BHQ2-AGATAAGTTCGCTGTATTCGGTGT-C$_3$

On 3:
(SEQ ID NO: 24)
5'-Cal Red 590-AAACGATTGGGGACTTTAATTGGGAGTTT-BHQ2

Off 3:
(SEQ ID NO: 25)
5'-AGACGTCTTATGTTGTAATTAT-BHQ2

On 4:
(SEQ ID NO: 26)
5'-Cal Red 590-TTTGTAAAGAATGCGTAGAGATAGGAGAA-BHQ2

Off 4:
(SEQ ID NO: 27)
5'-GAGGCATTGTTCACGTCGTTTGTTA-BHQ2

On 5a:
(SEQ ID NO: 28)
5'-BHQ2-TTTTTATACGTACGGCAATTACATCTGAA-Cal Red 590

Off 5a:
(SEQ ID NO: 29)
5'-BHQ2-TTTTTAAATTTAATATGGGGATAGC-C$_3$

On 5b:
(SEQ ID NO: 30)
5'-BHQ2-AGTGACCATAATATACCTCCGGCT-Cal Red 590

Off 5b:
(SEQ ID NO: 31)
5'-BHQ2-TCGTATAGTGGTCAATGTGGTATGG-C$_3$

-continued

```
ND1 Probes
On 1:
                                                          (SEQ ID NO: 32)
5'-Cal Orange 560-AAGTTCGGTTGGTTTTTGCTGGTGTGGTT-BHQ1

Off 1:
                                                          (SEQ ID NO: 33)
5'-TTCGGCAATGTCGAGGGGG-BHQ1

On 2:
                                                          (SEQ ID NO: 34)
5'-BHQ1-AATATGAAGAATAGAGCGAAGAGGCCTTT-Cal Orange 560

Off 2:
                                                          (SEQ ID NO: 35)
5'-BHQ1-GCGGCCTATTCCATGTTGACGCCTG-C3

On 3:
                                                          (SEQ ID NO: 36)
5'-BHQ1-TTAAGGTTGTAGTGATGGGGTGTTTAAA-Cal Orange 560

Off 3:
                                                          (SEQ ID NO: 37)
5'-BHQ1-TTATAATAATCTTTGTGTTTTCGGC-C3

On 4:
                                                          (SEQ ID NO: 38)
5'-BHQ1-AATTGATCAAGGGGTTTGGTATAGGGATT-Cal Orange 560

Off 4:
                                                          (SEQ ID NO: 39)
5'-BHQ1-GGGAGGTTTATAGTAAAAGAGAGAT-C3

On 5:
                                                          (SEQ ID NO: 40)
5'-BHQ1-TTAGATAAACCATAGTATGTCCGAGGGAA-Cal Orange 560

Off 5:
                                                          (SEQ ID NO: 41)
5'-BHQ1-TCATGATTGCAGTAGTGGTAAGAGG-C3
```

A three carbon linker is denoted with $C_3$ while Black Hole Quencher 1 and 2 are denoted by BHQ1 and BHQ2 (Biosearch Technologies, Novato Calif.). Underlined bases are those that are mismatched to the Anderson Sequence.

The DNA from HepG2 (hepatocellular carcinoma) or CCD-1112Sk (foreskin fibroblast) cells was extracted by placing 1 µl of cell suspension (on average 1000 cells) into 14 µl volume of a lysis buffer containing 100 µg/ml proteinase K, 10 mM Tris-Cl pH 8.3, and 5 µM SDS (sodium-dodecyl-sulfate); heating to 50° C. for 2 hours followed by 95° C. for 15 minutes. The samples were then stored at −20° C.

Before PCR amplification, the mtDNA was linearized by restriction digest with BamH1 (Roche, Mannheim, Germany). Digestion was carried out in a 20 µl volume consisting of 1×PCR buffer (Invitrogen, Carlsbad, Calif.), 1.5 mM $MgCl_2$, 10 µl mtDNA, and 10 units of BamH1. The reaction was heated to 37° C. for 1 hour followed by 65° C. for 15 minutes. The samples were then stored at −20° C.

LATE-PCR amplifications were carried out in a 25 µl volume consisting of 1×PCR buffer (Invitrogen, Carlsbad, Calif.), 3 mM $MgCl_2$, 250 nM dNTPs, 50 nM Limiting Primer, 1000 nM Excess Primer (HV2), 100 nM Limiting Primer, 1000 nM Excess Primer (CO2), 50 nM Limiting Primer, 1500 nM Excess Primer (ND1), 2.5 units of Platinum Taq DNA Polymerase (Invitrogen, Carlsbad, Calif.), 50 nM of the on probes, and 15 nM of the off probes. For each bulk sample tested, approximately 1000 genome equivalents were used. For mutational analysis, fewer than ten genome equivalents were used. Amplification reactions for each sequence were run in triplicate.

The thermal profile for the amplification reaction was as follows: 95° C./3 min for 1 cycle, followed by 95° C./5 s—65° C./45 s—72° C./90 s for 65 cycles, for bulk analysis and 75 cycles for low copy analysis, followed by a single cycle of 75° C. for 10 min and a single cycle of 25° C. for 10 min. The reaction products were characterized by the use of melt profile analysis. Fluorescent acquisition of the probe signals was carried out at each degree in a melt starting at 25° C. with 1° C. increments at 45 s intervals to 80° C.

Figure 4A:
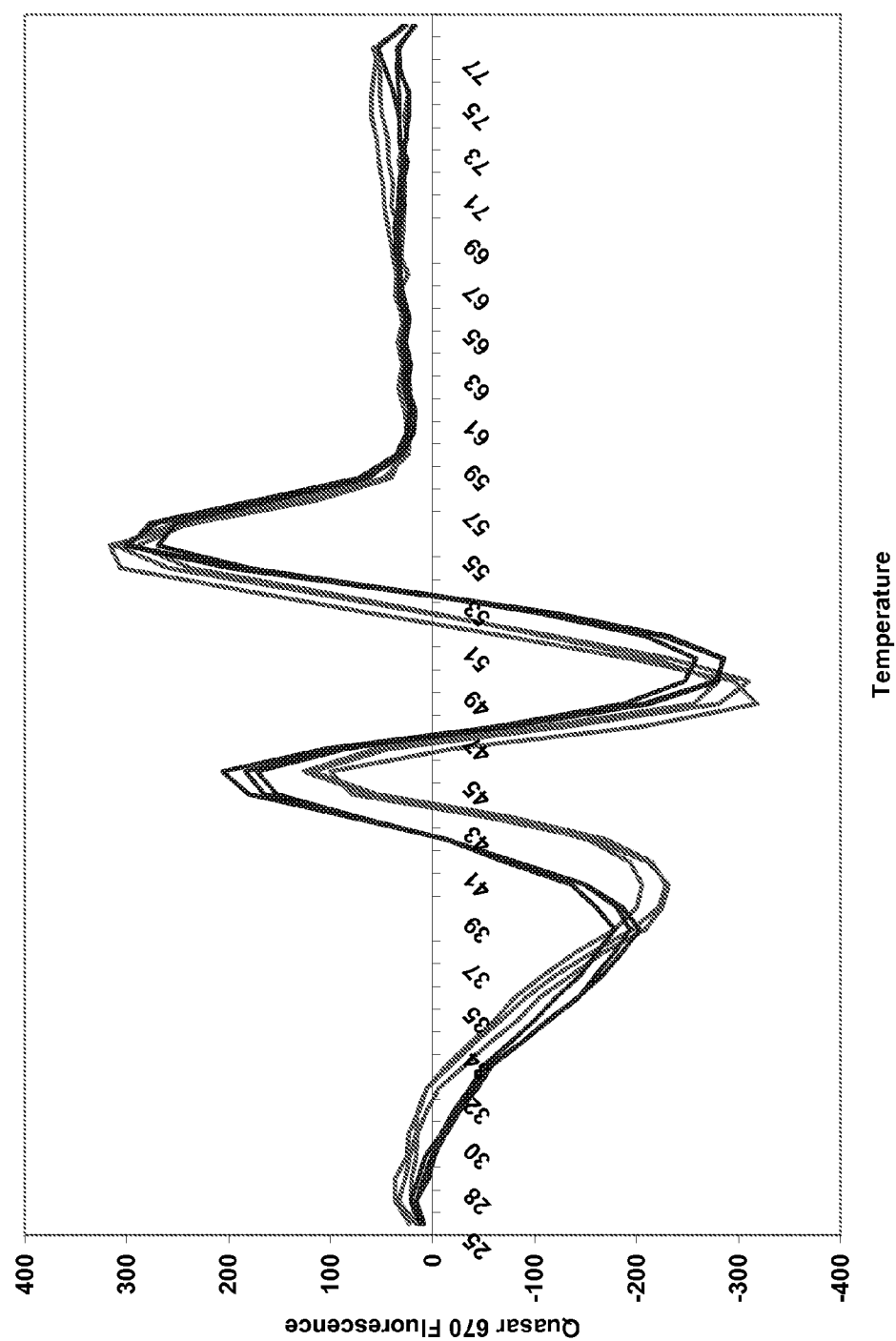
FIG. 4 shows first derivative fluorescence signatures of three target sequences within the following three human mitochondrial genes: (A) the Hypervariable Region 2 of the D-loop, HV2, (B) the Cytochrome C Oxidase Subunit 2 gene, CO2 (also abbreviated at COX2), and (C) the NADH dehydrogenase subunit 1 gene, ND1. The fluorescent signature for a HepG2 cell line are shown in the color red and the fluorescent signaturatures for a skin fibroblast cell line are shown in blue.
Figure 4B:
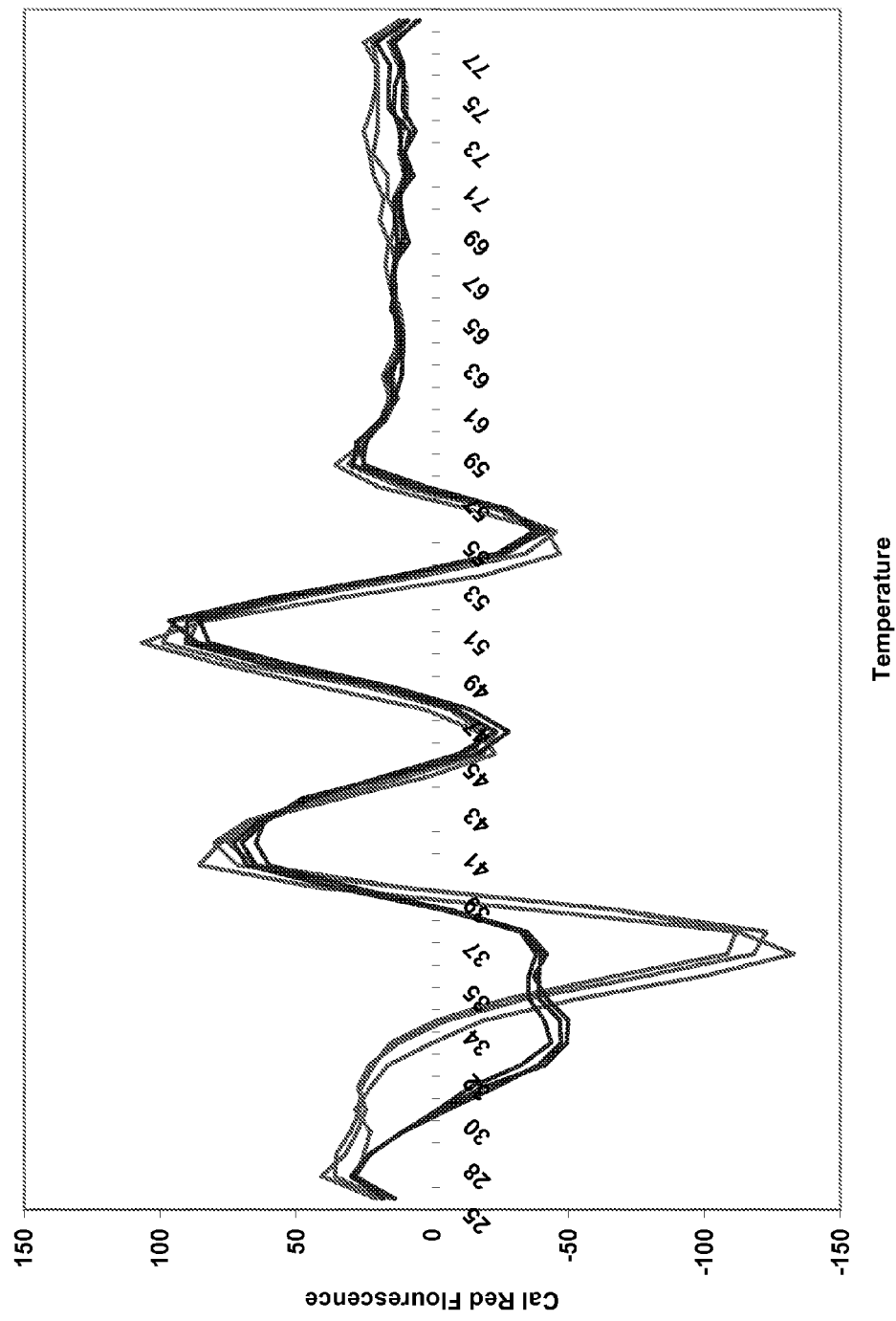
Figure 4C:
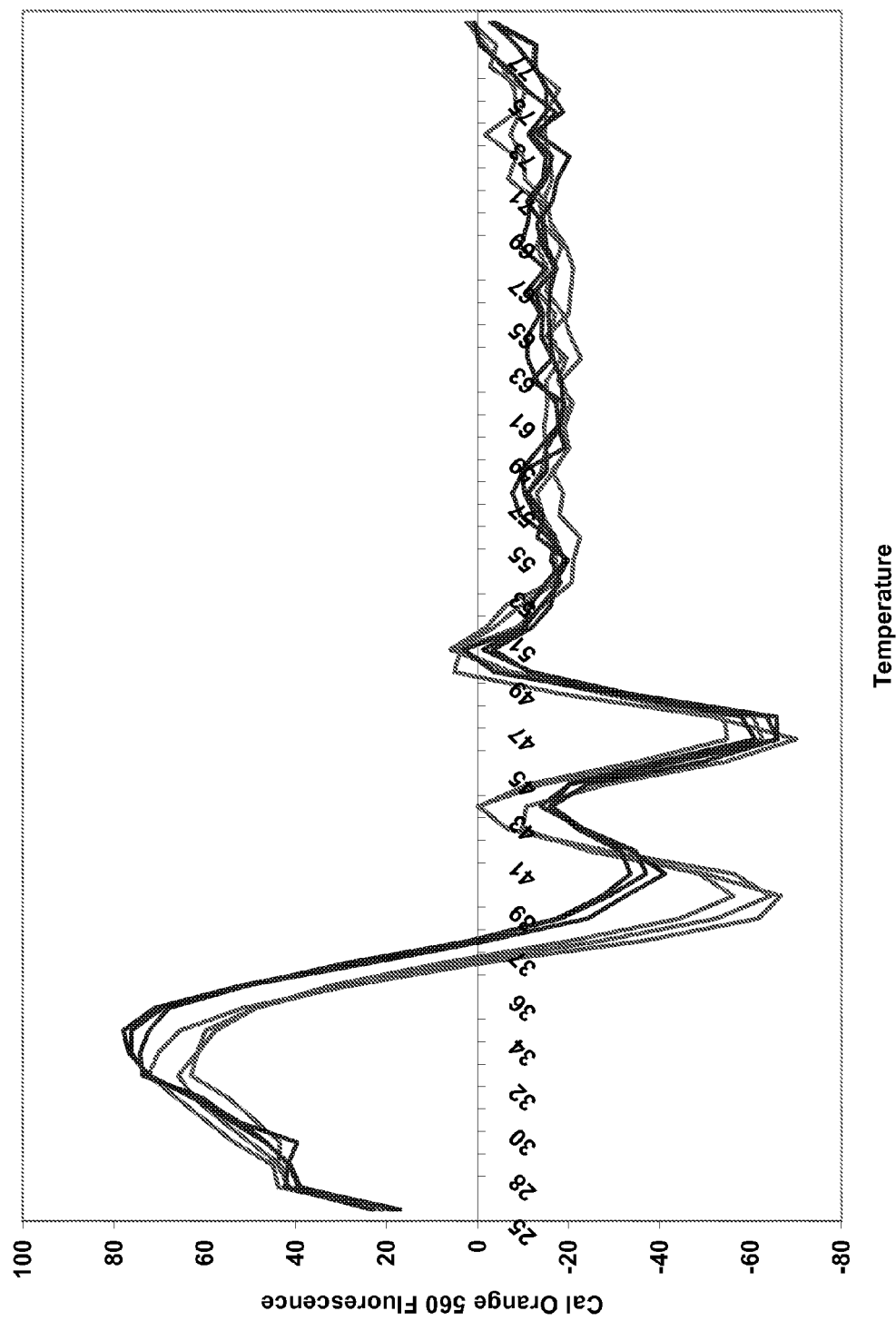
Figure 5A:
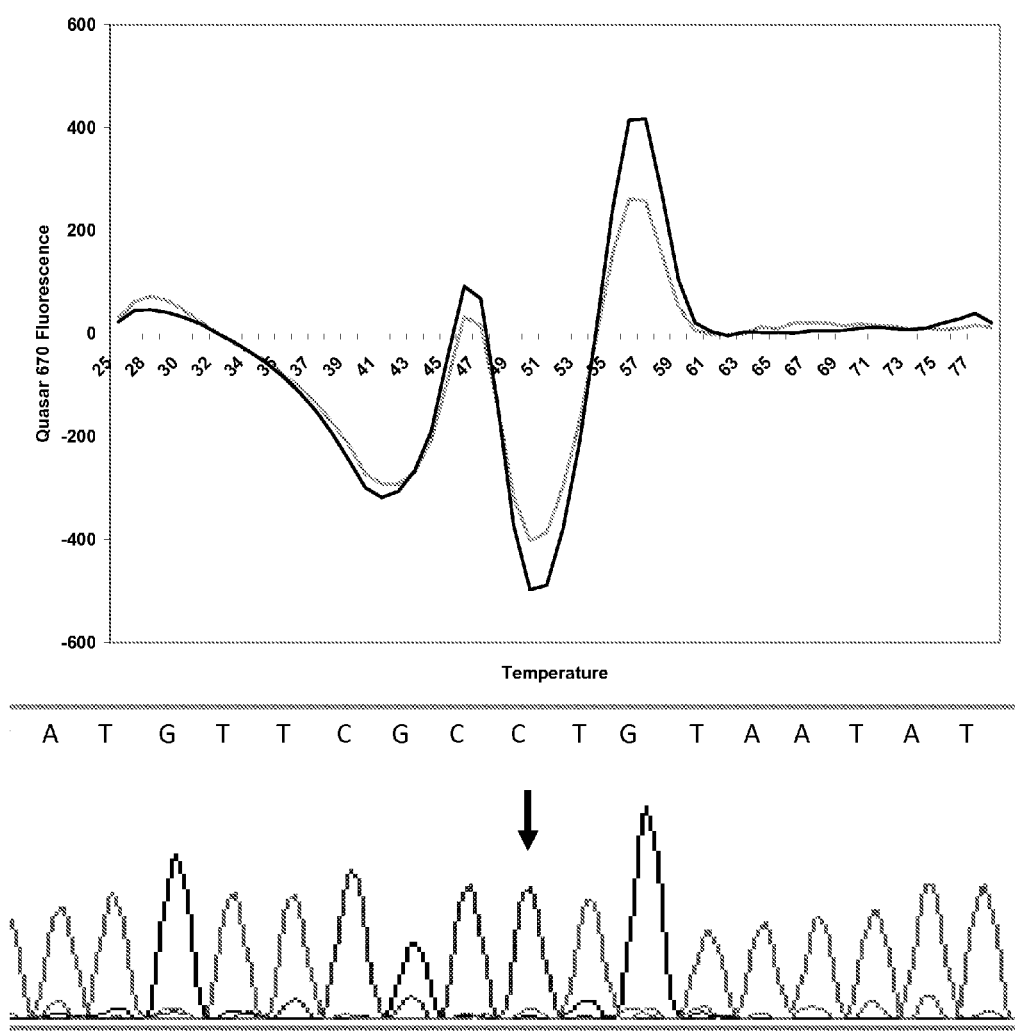
FIG. 5 shows two examples A and B of first derivative plots of consensus fluorescent signatures generated by amplification of a large population of mtDNA molecules, black lines, or single mtDNA molecules, green, lines. Both examples are for the amplified HV2 target in HepG2 cells. The lower part of the figure shows the nucleotide sequence for the consensus amplicons and the single molecule amplicons. Arrows in the sequencing below each graph indicates the base that is changed and accounts for the change in the fluorescent signature in example B.
Figure 5B:
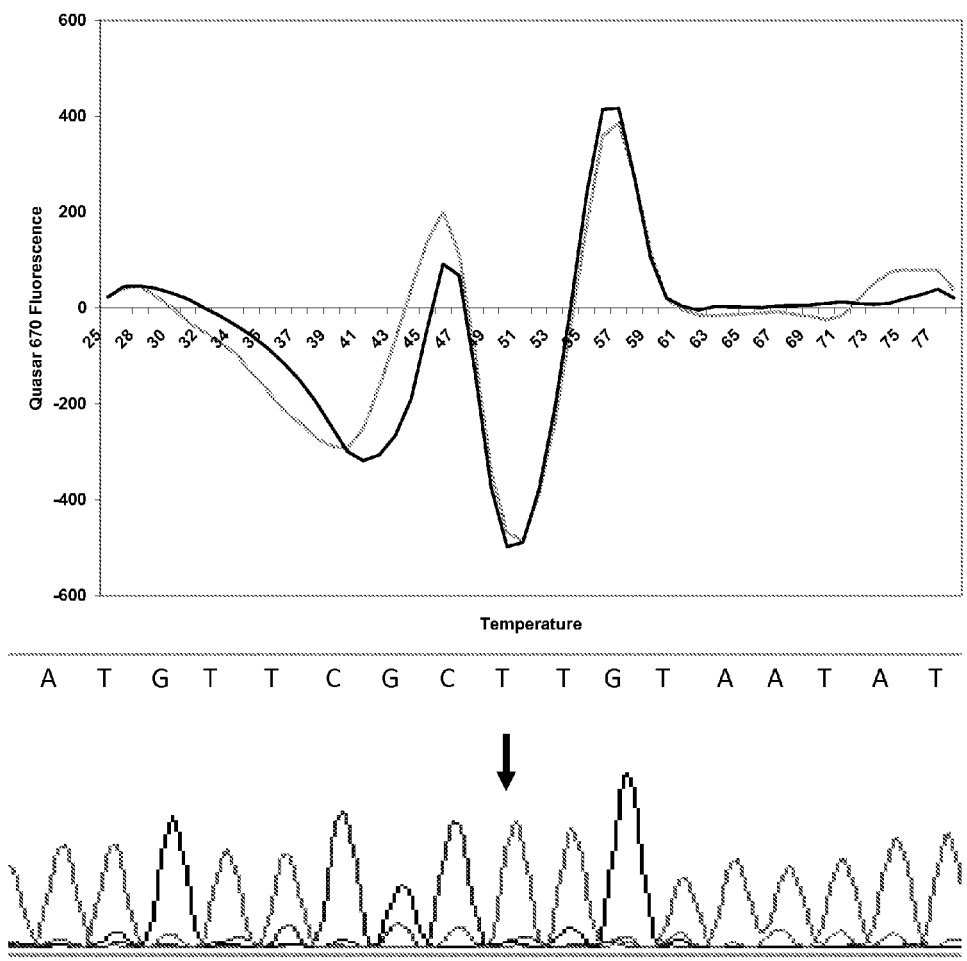
Figure 6A:
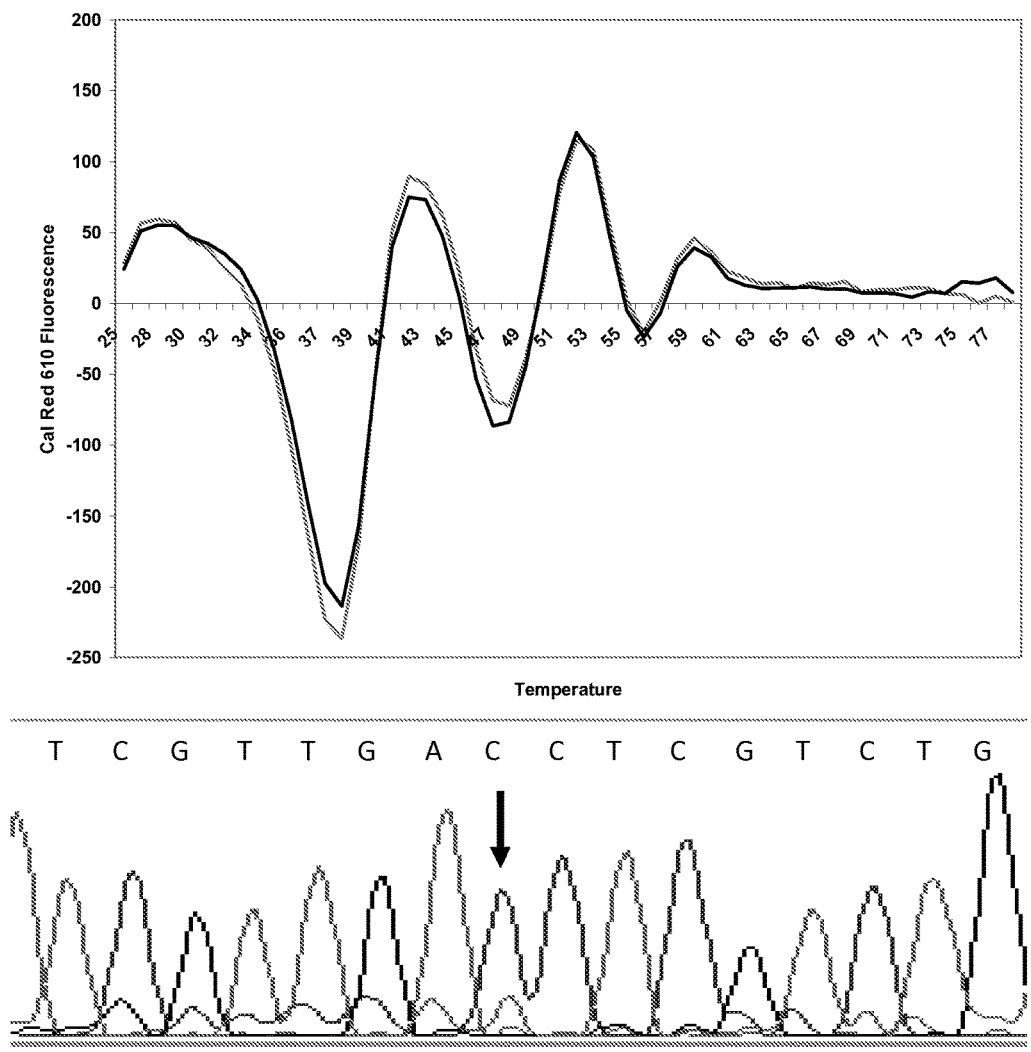
FIG. 6 shows two examples A and B of first derivative plots of consensus fluorescent signatures generated by amplification of a large population of mtDNA molecules, black lines, or single mtDNA molecules, green, lines. Both examples are for the amplified CO2 target in HepG2 cells. The lower part of the figure shows the nucleotide sequence for the consensus amplicons and the single molecule amplicons. Arrows in the sequencing below each graph indicates the base that is changed and accounts for the change in the fluorescent signature in example B.
Figure 6B:
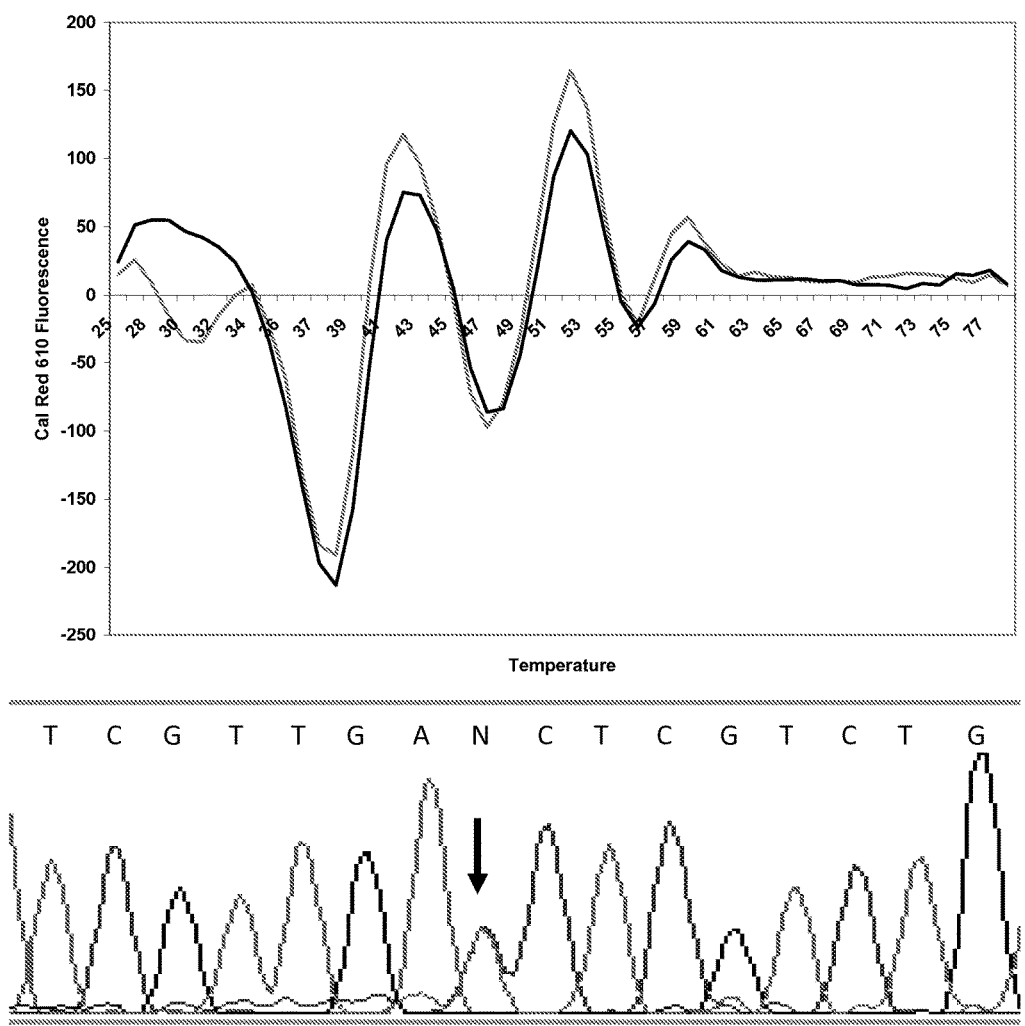

Graphs depicting fluorescence profiles obtained from the assay described above are depicted in FIGS. 4-6.

Various modification, recombination, and variation of the described features and embodiments will be apparent to those skilled in the art without departing from the scope and spirit of the invention. Although specific embodiments have been described, it should be understood that the claims should not be unduly limited to such specific embodiments. Indeed, various modifications of the described modes and embodiments that are obvious to those skilled in the relevant fields are intended to be within the scope of the following claims, and can be made without departing from the the inventive concepts described herein.

All publications and patents listed below and mentioned in the present application are herein incorporated by reference in their entireties.

REFERENCES

1.) Anderson, S., A. T. Bankier, B. G. Barrell, M. H. L. De Bruijn, A. R. Coulson, et al. (1981) "Sequence and Organization of the Human Mitochondrial Genome." Nature 290. pp. 457-465.

2.) Andrews, R. M., I. Kubacka, P. F. Chinnery, R. N. Lightowlers, D. M. Turnbull, et al. (1999) "Reanalysis and revision of the Cambridge reference sequence for human mitochondrial." Nature Genetics 23. pp. 147.
3.) Wallace, Douglas C. (1994) "Mitochondrial DNA sequence variation in human evolution and disease." Proceedings of the National Academy of Science, 91. pp. 8739-8746.
4.) Pravenec, Michal, Masaya Hyakukoku, Josef Houstek, Vaclav Zidek, Vladimir Landa, et al. (2007) "Direct Linkage of Mitochondrial Genome Variation to Risk Factors for Type 2 Diabetes in Conplastic Strains." Genome Research, 17. pp. 1319-1326.
5.) Swerdlow, Russell H. and Shaharyar M. Khan. (2004) "A 'Mitochondrial Cascade Hypothesis' for Sporadic Alzheimer's Disease" Medical Hypotheses 63. pp. 8-20.
6.) Chen, Junjian and Fred F. Kadlubar. (2004) "Mitochondrial Mutagenesis and Oxidative Stress in Human Prostate Cancer." Journal of Environmental Science and Health, C22. pp. 1-12.
7.) He, Yiping et al. (2010) Heteroplasmic mitochondrial DNA mutations in normal and tumour cells. Nature 464, 610-614.
8.) Onyango, Isaac, Khan, Shaharyar, Miller, Bradley, Swerdlow, Russell, Trimmer, Patricia, and Bennett, James. (2006) Mitochondrial genomic contribution to mitochondrial dysfunction in Alzheimer's disease. Journal of Alzheimer's Disease 9, 183-193.
9.) Fleischman et al. (2007) Effects of a nucleoside reverse transcriptase inhibitor, stavudine, on glucose disposal and mitochondrial function in muscle of healthy adults. American Journal of Physiology-Endocrinology and Metabolism 292, 1666-1673.
10.) Martin, Annalise M. et al (2003) Accumulation of Mitochondrial DNA Mutations in Human Immunodeficiency Virus-Infected Patients Treated with Nucleoside-Analogue Reverse-Transcriptase Inhibitors. American Journal of Human Genetics 72, 549-560.
11.) Cote, Helene C. F., et al. (2002) Changes in mitochondrial DNA as a marker of nucleoside toxicity in HIV-infected patients. New England Journal of Medicine 346, 811-820.
12.) Arnaudo, E., et al. (1991) Depletion of muscle mitochondrial DNA in AIDS patients with zidovudine-induced myopathy. Lancet 337, 508-510.
13.) Wendelsdorf K V, Song Z, Cao Y, Samuels D C (2009) An Analysis of Enzyme Kinetics Data for Mitochondrial DNA Strand Termination by Nucleoside Reverse Transcription Inhibitors. PLoS Comput Biol 5(1): e1000261. doi:10.1371/journal.pcbi.1000261
14.) Yiping et al. (2010) Heteroplasmic mitochondrial DNA mutations in normal and tumour cells. Nature 464, 610-616.
15.) Rice et al. (2007) Monoplex/multiplex linear-after-the-exponential-PCR assays combined with PrimeSafe and Dilute-'N'-Go sequencing. Nature Protocols 2 (10), 2429-2438.
16.) Osborne et al. (2009) Single-Molecule LATE-PCR Analysis of Human Mitochondrial Genomic Sequence Variations. PLOS One 4 (5) e5636.

We claim:

1. A method for detecting mutations in mitochondrial DNA (mtDNA), chloroplastic DNA (cpDNA), or plasmid DNA, comprising
a) providing:
   i) a sample comprising mtDNA, cpDNA, and/or plasmid DNA, and
   ii) detection reagents comprising at least one pair of primers configured to amplify a target region of said mtDNA, cpDNA or plasmid DNA, and at least two detectably distinguishable probe sets of a signaling probe and an associated quencher probe which hybridize to adjacent sequences in said target region, the signaling probe comprising a fluorescence-emitting fluorophore and the quencher probe comprising a non-fluorescent quencher, wherein said signaling probe does not emit fluorescence above background when not hybridized to its target sequence and wherein when both the signaling probe and the associated quencher probe and are hybridized to the adjacent sequences in the target region the quencher probe quenches a fluorescent signal emitted by the fluorescence-emitting fluorophore of the signaling probe,
   wherein the at least two probe sets comprise at least one probe that is part of both of the two probe sets, said probe:
      comprising a quencher on each end, each end interacting with a different signaling probe from the at least two probe sets when both of the at least two probe sets are hybridized to the target region, or
      comprising a fluorophore on one end and a quencher on the other end, the fluorophore interacting with a quencher probe in one of the at least two probe sets and the quencher interacting with a signaling probe of the other of the at least two probe sets when both of the at least two probe sets are hybridized to the target region;
b) amplifying said target region of said mtDNA, cpDNA, or plasmid DNA with said primers by a non-symmetric amplification method;
c) detecting the fluorescence of said fluorescence-emitting dye from each detectably distinguishable probe set at a range of temperatures;
d) generating temperature-dependent fluorescence signatures for each fluorescence-emitting dye; and
e) analyzing said temperature-dependent fluorescence signatures to detect mutations in said mtDNA, cpDNA or plasmid DNA.

2. The method of claim 1, wherein said fluorescence-emitting fluorophore and said non-fluorescent quenchers of each probe set are capable of interacting by FRET.

3. The method of claim 1, wherein the degree of complementarity between the probes of said probe sets and their target sequence varies based on the number of mutations in said target sequence, and wherein said different degrees of complementarity result in different temperature-dependent fluorescent signatures generated by said probe set and said target sequences.

4. The method of claim 1, wherein detecting mutations in mtDNA comprises detecting mutations in one or more of the HV2, CO2, and ND1 regions of mtDNA.

5. A reagent kit for detecting one or more mutations in a target region of mtDNA, cpDNA, or plasmid DNA comprising:
   a) at least one pair of primers, wherein said primers are configured bind to and amplify said target region of mtDNA, cpDNA or plasmid DNA; and
   b) at least two detectably distinguishable probe sets of a signaling probe and an associated quencher probe which hybridize to adjacent sequences in said target region, the signaling probe comprising a fluorescence-emitting fluorophore and the quencher probe comprising a non-fluorescent quencher, wherein said signaling probe does not emit fluorescence above background when not hybridized to its target sequence and wherein when both the signaling probe and the associated quencher probe and are hybridized to the adjacent sequences in the target region the quencher probe quenches a fluorescent signal emitted by the fluorescence-emitting fluorophore of the signaling probe,
   wherein the at least two probe sets comprise at least one probe that is part of both of the two probe sets, said probe:
      comprising a quencher on each end, each end interacting with a different signaling probe from the at least two probe sets when both of the at least two probe sets are hybridized to the target region, or
      comprising a fluorophore on one end and a quencher on the other end, the fluorophore interacting with a quencher probe in one of the at least two probe sets and the quencher interacting with a signaling probe of the other of the at least two probe sets when both of the at least two probe sets are hybridized to the target region.

6. The reagent kit of claim 5, wherein the melting temperature of the signaling probe in at least one of the at least two probe sets is higher than the melting temperature of the associated quencher probe in the same probe set.

7. The reagent kit of claim 5, wherein said fluorescence-emitting fluorophore and said non-fluorescent quenchers of each probe set are capable of interacting by FRET.

8. The reagent kit of claim 5, wherein said reagent kit comprises 5 or more probe sets.

9. The reagent kit of claim 5, wherein the degree of complementarity between the probes of said probe sets and their target sequence varies based on the number of mutations in said target sequence.

10. The reagent kit of claim 5, wherein the probes in said at least one detectably distinguishable probe set have melting temperatures with their target nucleic acid sequences below the annealing temperature of at least one primer of the amplification reaction.

11. The reagent kit of claim 5, wherein one or more detectably distinguishable probe sets are configured to hybridize to the HV2 region, CO2 region, or ND1 region of mtDNA.

12. The reagent kit of claim 11, wherein at least one of said detectably distinguishable probe sets are selected from one or more of:
   (a) SEQ ID NO:10 and SEQ ID NO:11;
   (b) SEQ ID NO:12 and SEQ ID NO:13;
   (c) SEQ ID NO:14 and SEQ ID NO:15;
   (d) SEQ ID NO:16 and SEQ ID NO:17;
   (e) SEQ ID NO:18 and SEQ ID NO:19;
   (f) SEQ ID NO:20 and SEQ ID NO:21;
   (g) SEQ ID NO:22 and SEQ ID NO:23;
   (h) SEQ ID NO:24 and SEQ ID NO:25;
   (i) SEQ ID NO:26 and SEQ ID NO:27;
   (j) SEQ ID NO:28 and SEQ ID NO:29;
   (k) SEQ ID NO:30 and SEQ ID NO:31;
   (l) SEQ ID NO:32 and SEQ ID NO:33;
   (m) SEQ ID NO:34 and SEQ ID NO:35;
   (n) SEQ ID NO:36 and SEQ ID NO:37;
   (o) SEQ ID NO:38 and SEQ ID NO:39; and
   (p) SEQ ID NO:40 and SEQ ID NO:41.

13. The reagent kit of claim 11, wherein said one or more primer pairs comprise:
   (a) SEQ ID NO.:1 and SEQ ID NO.:2;
   (b) SEQ ID NO.:3 and SEQ ID NO.:4; and
   (c) SEQ ID NO.:5 and SEQ ID NO.:6.

14. The reagent kit of claim 5, further comprising one or more additional oligonucleotides configured to suppress mis-priming during amplification reactions.

15. A method for detecting not previously known mutations in a target nucleic acid sequence, comprising
   a) providing:
      i) a sample comprising target nucleic acid, and
      ii) detection reagents comprising at least one pair of primers configured to amplify a target region of said target nucleic acid sequence, and at least two detectably distinguishable probe sets of a signaling probe and an associated quencher probe which hybridize to adjacent sequences in said target region, the signaling probe comprising a fluorescence-emitting fluorophore and the quencher probe comprising a non-fluorescent quencher, wherein said signaling probe does not emit fluorescence above background when not hybridized to its target sequence and wherein when both the signaling probe and the associated quencher probe and are hybridized to the adjacent sequences in the target region the quencher probe quenches a fluorescent signal emitted by the fluorescence-emitting fluorophore of the signaling probe,
      wherein the at least two probe sets comprise at least one probe that is part of both of the two probe sets, said probe:
         comprising a quencher on each end, each end interacting with a different signaling probe from the at least two probe sets when both of the at least two probe sets are hybridized to the target region, or
         comprising a fluorophore on one end and a quencher on the other end, the fluorophore interacting with a quencher probe in one of the at least two probe sets and the quencher interacting with a signaling probe of the other of the at least two probe sets when both of the at least two probe sets are hybridized to the target region;
   b) amplifying said target region of said target nucleic acid sequence with said primers;
   c) detecting the fluorescence of said fluorescence-emitting dye from each detectably distinguishable probe set at a range of temperatures;

d) generating temperature-dependent fluorescence signatures for each fluorescence-emitting dye; and
e) analyzing said temperature-dependent fluorescence signatures to detect at least one previously unknown mutation in said target nucleic acid sequence.

* * * * *

SEQUENCE LISTING

```
<160> NUMBER OF SEQ ID NOS: 75

<210> SEQ ID NO 1
<211> LENGTH: 28
<212> TYPE: DNA
<213> ORGANISM: Artificial Sequence
<220> FEATURE:
<223> OTHER INFORMATION: Synthetic

<400> SEQUENCE: 1
aaagcggtgt gtgtgtgctg ggtaggat                                           28

<210> SEQ ID NO 2
<211> LENGTH: 27
<212> TYPE: DNA
<213> ORGANISM: Artificial Sequence
<220> FEATURE:
<223> OTHER INFORMATION: Synthetic

<400> SEQUENCE: 2
acttcagggt cataaagcct aaatagc                                            27

<210> SEQ ID NO 3
<211> LENGTH: 31
<212> TYPE: DNA
<213> ORGANISM: Artificial Sequence
<220> FEATURE:
<223> OTHER INFORMATION: Synthetic

<400> SEQUENCE: 3
aatagagggg gtagaggggg tgctataggg t                                       31

<210> SEQ ID NO 4
<211> LENGTH: 28
```

```
<212> TYPE: DNA
<213> ORGANISM: Artificial Sequence
<220> FEATURE:
<223> OTHER INFORMATION: Synthetic

<400> SEQUENCE: 4
tccttatctg cttcctagtc ctgtatgc                                          28

<210> SEQ ID NO 5
<211> LENGTH: 37
<212> TYPE: DNA
<213> ORGANISM: Artificial Sequence
<220> FEATURE:
<223> OTHER INFORMATION: Synthetic

<400> SEQUENCE: 5
aacataagaa cagggaggtt agaagtaggg tcttggt                                37

<210> SEQ ID NO 6
<211> LENGTH: 18
<212> TYPE: DNA
<213> ORGANISM: Artificial Sequence
<220> FEATURE:
<223> OTHER INFORMATION: Synthetic

<400> SEQUENCE: 6
cgccccgacc ttagctct                                                     18

<210> SEQ ID NO 7
<211> LENGTH: 590
<212> TYPE: DNA
<213> ORGANISM: Homo sapiens

<400> SEQUENCE: 7
gctcgccaca cacacacgac ccatcctacc cgcccccaac ataactactc taatcatcat       60
accctcaccc tccccttta ttacacaatc aaccccccac tgacaatttt cacgtatggc       120
ggttttctat tttaaacttt agaccaatcc gaccacaatc ccaagaaaca aaacccccaa      180
accgtctcta cacaaattca cgacaccggt cttcgccccc tcccccccaa accaccttta     240
aaaaacaata ctacagacac acctttcacc gacacgtctg taagttaaca ataataatac      300
aggatgttcg taattaatta attgtgtgaa atcattcata caagcggaca ttataacttg      360
catccacgct atttattatc ctactccgtc cttagtttct gtctatgacg ctgtatccca      420
cgaggccgag gtcgcagagc gttacgatag cgcacgtatg gggggtctgc ttttatggtt      480
tacgtacctc tcgagggcac tcaccaatta tcccactatc tggacactag gtagcactac      540
agaataaatt cccccttgcac acccgataaa tccgaaatac tgggacttca                590

<210> SEQ ID NO 8
<211> LENGTH: 616
<212> TYPE: DNA
<213> ORGANISM: Homo sapiens

<400> SEQUENCE: 8
cccgagatct cccccatctc ccccacgata tcccatttat gcccgggata aagtttctaa       60
aaatcccctt aattaagatc ctgctacccg tactttgaca ccaaacgagg tgtctaaagt      120
ctcgtaactg gcatcatatg ggggccagca catcgccact ttcaccaaac caaatctgca     180
ggcccttaac gtagacaaaa attcggatta caccctgtc gagtactcac gttctgcaga      240
acactacatt aataatatgc ttaccccga agttagccct catgatgagc taacagttgc      300
```

```
agttcctcag cgtccagcgg accaagatcc ttattacccc cttcatacat cctcaacttc    360
taatcaggcg gcatcagcca catgagcatc caagtcatgg taaccaccgg ttaactaaac    420
taccattccc tccctagcaa ctggagcaga caatacattt cctacgcatc cctaccctcc    480
cgctactcct gatcctacta ccgcccgtcc tatcaagtct gccaaagata aaggactcgc    540
agactctaca atcataatca atcaaaacaa cactcacaat ccttttcccg tatgtcctga    600
tccttcgtct attcct                                                   616
```

```
<210> SEQ ID NO 9
<211> LENGTH: 599
<212> TYPE: DNA
<213> ORGANISM: Homo sapiens

<400> SEQUENCE: 9
aagtattctt gtccctccaa tcttcatccc agaaccactg ttttatacaa cacatctcaa     60
gtcccctctc acgcagtata caacaaggat ccttctaaca tcaccactcc cacaaataat    120
attattacaa acacataagc cgatacttct tatcccgctt ccccggacgc cgcataagct    180
acaacttcgg actctgatca agcctgaggg gaagccgttc cagcttcccc caagccaacc    240
agagacgatc acacctctat ttagtataat accggttccc agtactaccg tcctcattag    300
tctccacaag aacacaacac tattcccacc tctccaattt cctcggtgaa taatcattac    360
aactatcatc ttactaccga tcccactgaa gtatactcta caaacccga tgacgagcgt    420 cacgcggcta gtcccgcatc aaactcaaac tacgagtggg actagtctcc taactcattt    480
gccgatccga tctccaccga tcttatttat cctccggatc caactccaac tggtccccca    540
acccataccc ctccccccaa gtatcatctt ctcgctacca ctctcgattc cagcccgc     599
```

```
<210> SEQ ID NO 10
<211> LENGTH: 28
<212> TYPE: DNA
<213> ORGANISM: Artificial Sequence
<220> FEATURE:
<223> OTHER INFORMATION: Synthetic

<400> SEQUENCE: 10
tggttagggt tctttatttt ggggttca                                       28
```

```
<210> SEQ ID NO 11
<211> LENGTH: 24
<212> TYPE: DNA
<213> ORGANISM: Artificial Sequence
<220> FEATURE:
<223> OTHER INFORMATION: Synthetic

<400> SEQUENCE: 11
aatgtgaaat ctgcttgggc tggt                                           24
```

```
<210> SEQ ID NO 12
<211> LENGTH: 29
<212> TYPE: DNA
<213> ORGANISM: Artificial Sequence
<220> FEATURE:
<223> OTHER INFORMATION: Synthetic

<400> SEQUENCE: 12
aatggcagag atgtctttaa gtgctgttt                                      29
```

```
<210> SEQ ID NO 13
<211> LENGTH: 25
```

```
<212> TYPE: DNA
<213> ORGANISM: Artificial Sequence
<220> FEATURE:
<223> OTHER INFORMATION: Synthetic

<400> SEQUENCE: 13
ggctaggagt tggggagggc gggtt                                            25

<210> SEQ ID NO 14
<211> LENGTH: 29
<212> TYPE: DNA
<213> ORGANISM: Artificial Sequence
<220> FEATURE:
<223> OTHER INFORMATION: Synthetic

<400> SEQUENCE: 14
aaatgtaatc gcgttcatat cacccagtt                                        29

<210> SEQ ID NO 15
<211> LENGTH: 25
<212> TYPE: DNA
<213> ORGANISM: Artificial Sequence
<220> FEATURE:
<223> OTHER INFORMATION: Synthetic

<400> SEQUENCE: 15
acgagagtac ccaacgcatg gagag                                            25

<210> SEQ ID NO 16
<211> LENGTH: 29
<212> TYPE: DNA
<213> ORGANISM: Artificial Sequence
<220> FEATURE:
<223> OTHER INFORMATION: Synthetic

<400> SEQUENCE: 16
taattgaaca taggtacgat aaataatta                                        29

<210> SEQ ID NO 17
<211> LENGTH: 25
<212> TYPE: DNA
<213> ORGANISM: Artificial Sequence
<220> FEATURE:
<223> OTHER INFORMATION: Synthetic

<400> SEQUENCE: 17
tttagtaaat gtgttcacct gtaat                                            25

<210> SEQ ID NO 18
<211> LENGTH: 29
<212> TYPE: DNA
<213> ORGANISM: Artificial Sequence
<220> FEATURE:
<223> OTHER INFORMATION: Synthetic

<400> SEQUENCE: 18
aactgggtga aaagtgacta tgcggactt                                        29

<210> SEQ ID NO 19
<211> LENGTH: 25
<212> TYPE: DNA
<213> ORGANISM: Artificial Sequence
<220> FEATURE:
<223> OTHER INFORMATION: Synthetic

<400> SEQUENCE: 19
```
tgggggaagt tttttcttat tatgt                                25

<210> SEQ ID NO 20
<211> LENGTH: 29
<212> TYPE: DNA
<213> ORGANISM: Artificial Sequence
<220> FEATURE:
<223> OTHER INFORMATION: Synthetic

<400> SEQUENCE: 20
aaactactcg attatcaacg tcaaggatt                            29

<210> SEQ ID NO 21
<211> LENGTH: 25
<212> TYPE: DNA
<213> ORGANISM: Artificial Sequence
<220> FEATURE:
<223> OTHER INFORMATION: Synthetic

<400> SEQUENCE: 21
gtcgcaggac gcctagtttt aggaa                                25

<210> SEQ ID NO 22
<211> LENGTH: 29
<212> TYPE: DNA
<213> ORGANISM: Artificial Sequence
<220> FEATURE:
<223> OTHER INFORMATION: Synthetic

<400> SEQUENCE: 22
aaaatggggg aagtttgtat gagttgatt                            29

<210> SEQ ID NO 23
<211> LENGTH: 24
<212> TYPE: DNA
<213> ORGANISM: Artificial Sequence
<220> FEATURE:
<223> OTHER INFORMATION: Synthetic

<400> SEQUENCE: 23
agataagttc gctgtattcg gtgt                                 24

<210> SEQ ID NO 24
<211> LENGTH: 29
<212> TYPE: DNA
<213> ORGANISM: Artificial Sequence
<220> FEATURE:
<223> OTHER INFORMATION: Synthetic

<400> SEQUENCE: 24
aaacgattgg ggactttaat tgggagttt                            29

<210> SEQ ID NO 25
<211> LENGTH: 22
<212> TYPE: DNA
<213> ORGANISM: Artificial Sequence
<220> FEATURE:
<223> OTHER INFORMATION: Synthetic

<400> SEQUENCE: 25
agacgtctta tgttgtaatt at                                   22

<210> SEQ ID NO 26
<211> LENGTH: 29
<212> TYPE: DNA
<213> ORGANISM: Artificial Sequence
<220> FEATURE:
<223> OTHER INFORMATION: Synthetic

<400> SEQUENCE: 26
tttgtaaaga atgcgtagag ataggagaa                           29

<210> SEQ ID NO 27
<211> LENGTH: 25
<212> TYPE: DNA
<213> ORGANISM: Artificial Sequence
<220> FEATURE:
<223> OTHER INFORMATION: Synthetic

<400> SEQUENCE: 27
gaggcattgt tcacgtcgtt tgtta                               25

<210> SEQ ID NO 28
<211> LENGTH: 29
<212> TYPE: DNA
<213> ORGANISM: Artificial Sequence
<220> FEATURE:
<223> OTHER INFORMATION: Synthetic

<400> SEQUENCE: 28
tttttatacg tacggcaatt acatctgaa                           29

<210> SEQ ID NO 29
<211> LENGTH: 25
<212> TYPE: DNA
<213> ORGANISM: Artificial Sequence
<220> FEATURE:
<223> OTHER INFORMATION: Synthetic

<400> SEQUENCE: 29
tttttaaatt taatatgggg atagc                               25

<210> SEQ ID NO 30
<211> LENGTH: 24
<212> TYPE: DNA
<213> ORGANISM: Artificial Sequence
<220> FEATURE:
<223> OTHER INFORMATION: Synthetic

<400> SEQUENCE: 30
agtgaccata atatacctcc ggct                                24

<210> SEQ ID NO 31
<211> LENGTH: 25
<212> TYPE: DNA
<213> ORGANISM: Artificial Sequence
<220> FEATURE:
<223> OTHER INFORMATION: Synthetic

<400> SEQUENCE: 31
tcgtatagtg gtcaatgtgg tatgg                               25

<210> SEQ ID NO 32
<211> LENGTH: 29
<212> TYPE: DNA
<213> ORGANISM: Artificial Sequence
<220> FEATURE:
<223> OTHER INFORMATION: Synthetic

<400> SEQUENCE: 32
aagttcggtt ggttttgct ggtgtggtt                            29

<210> SEQ ID NO 33
<211> LENGTH: 19
<212> TYPE: DNA
<213> ORGANISM: Artificial Sequence
<220> FEATURE:
<223> OTHER INFORMATION: Synthetic

<400> SEQUENCE: 33
ttcggcaatg tcgaggggg                                               19

<210> SEQ ID NO 34
<211> LENGTH: 29
<212> TYPE: DNA
<213> ORGANISM: Artificial Sequence
<220> FEATURE:
<223> OTHER INFORMATION: Synthetic

<400> SEQUENCE: 34
aatatgaaga atagagcgaa gaggcctttt                                   29

<210> SEQ ID NO 35
<211> LENGTH: 25
<212> TYPE: DNA
<213> ORGANISM: Artificial Sequence
<220> FEATURE:
<223> OTHER INFORMATION: Synthetic

<400> SEQUENCE: 35
gcggcctatt ccatgttgac gcctg                                        25

<210> SEQ ID NO 36
<211> LENGTH: 29
<212> TYPE: DNA
<213> ORGANISM: Artificial Sequence
<220> FEATURE:
<223> OTHER INFORMATION: Synthetic

<400> SEQUENCE: 36
ttaaggttgt agtgatgggg gtgtttaaa                                    29

<210> SEQ ID NO 37
<211> LENGTH: 25
<212> TYPE: DNA
<213> ORGANISM: Artificial Sequence
<220> FEATURE:
<223> OTHER INFORMATION: Synthetic

<400> SEQUENCE: 37
ttataataat ctttgtgttt tcggc                                        25

<210> SEQ ID NO 38
<211> LENGTH: 29
<212> TYPE: DNA
<213> ORGANISM: Artificial Sequence
<220> FEATURE:
<223> OTHER INFORMATION: Synthetic

<400> SEQUENCE: 38
aattgatcaa ggggtttggt atagggatt                                    29

<210> SEQ ID NO 39
<211> LENGTH: 25
<212> TYPE: DNA
<213> ORGANISM: Artificial Sequence
<220> FEATURE:
<223> OTHER INFORMATION: Synthetic

<400> SEQUENCE: 39
gggaggttta tagtaaaaga gagat                                         25

<210> SEQ ID NO 40
<211> LENGTH: 29
<212> TYPE: DNA
<213> ORGANISM: Artificial Sequence
<220> FEATURE:
<223> OTHER INFORMATION: Synthetic

<400> SEQUENCE: 40
ttagataaac catagtatgt ccgagggaa                                     29

<210> SEQ ID NO 41
<211> LENGTH: 25
<212> TYPE: DNA
<213> ORGANISM: Artificial Sequence
<220> FEATURE:
<223> OTHER INFORMATION: Synthetic

<400> SEQUENCE: 41
tcatgattgc agtagtggta agagg                                         25

<210> SEQ ID NO 42
<211> LENGTH: 24
<212> TYPE: DNA
<213> ORGANISM: Artificial Sequence
<220> FEATURE:
<223> OTHER INFORMATION: Synthetic

<400> SEQUENCE: 42
aaagcggtgt gtgtgtgctg ggta                                          24

<210> SEQ ID NO 43
<211> LENGTH: 24
<212> TYPE: DNA
<213> ORGANISM: Artificial Sequence
<220> FEATURE:
<223> OTHER INFORMATION: Synthetic

<400> SEQUENCE: 43
gttagggttc tttattttgg ggtt                                          24

<210> SEQ ID NO 44
<211> LENGTH: 25
<212> TYPE: DNA
<213> ORGANISM: Artificial Sequence
<220> FEATURE:
<223> OTHER INFORMATION: Synthetic

<400> SEQUENCE: 44
tggcagagat gtctttaagt gctgt                                         25

<210> SEQ ID NO 45
<211> LENGTH: 50
<212> TYPE: DNA
<213> ORGANISM: Artificial Sequence
<220> FEATURE:
<223> OTHER INFORMATION: Synthetic

<400> SEQUENCE: 45
ggctaggagt tggggagggc gggtttgggg gaagtttttt cttattatgt              50

<210> SEQ ID NO 46

```
<211> LENGTH: 25
<212> TYPE: DNA
<213> ORGANISM: Artificial Sequence
<220> FEATURE:
<223> OTHER INFORMATION: Synthetic

<400> SEQUENCE: 46
ctgggtgaaa agtgactatg cggac                                          25

<210> SEQ ID NO 47
<211> LENGTH: 25
<212> TYPE: DNA
<213> ORGANISM: Artificial Sequence
<220> FEATURE:
<223> OTHER INFORMATION: Synthetic

<400> SEQUENCE: 47
tttagtaaat gtgttcacct gtaat                                          25

<210> SEQ ID NO 48
<211> LENGTH: 25
<212> TYPE: DNA
<213> ORGANISM: Artificial Sequence
<220> FEATURE:
<223> OTHER INFORMATION: Synthetic

<400> SEQUENCE: 48
attgaacata ggtacgataa ataat                                          25

<210> SEQ ID NO 49
<211> LENGTH: 26
<212> TYPE: DNA
<213> ORGANISM: Artificial Sequence
<220> FEATURE:
<223> OTHER INFORMATION: Synthetic

<400> SEQUENCE: 49
aatgtaatcg cgttcatatc acccag                                         26

<210> SEQ ID NO 50
<211> LENGTH: 25
<212> TYPE: DNA
<213> ORGANISM: Artificial Sequence
<220> FEATURE:
<223> OTHER INFORMATION: Synthetic

<400> SEQUENCE: 50
acgagagtac ccaacgcatg gagag                                          25

<210> SEQ ID NO 51
<211> LENGTH: 31
<212> TYPE: DNA
<213> ORGANISM: Artificial Sequence
<220> FEATURE:
<223> OTHER INFORMATION: Synthetic

<400> SEQUENCE: 51
aatagagggg gtagaggggg tgctataggg t                                   31

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
```

```
tgaccataat atacctccgg                                              20

<210> SEQ ID NO 53
<211> LENGTH: 25
<212> TYPE: DNA
<213> ORGANISM: Artificial Sequence
<220> FEATURE:
<223> OTHER INFORMATION: Synthetic

<400> SEQUENCE: 53
tcgtatagtg gtcaatgtgg tatgg                                        25

<210> SEQ ID NO 54
<211> LENGTH: 25
<212> TYPE: DNA
<213> ORGANISM: Artificial Sequence
<220> FEATURE:
<223> OTHER INFORMATION: Synthetic

<400> SEQUENCE: 54
tttatacgta cggcaattac atctg                                        25

<210> SEQ ID NO 55
<211> LENGTH: 25
<212> TYPE: DNA
<213> ORGANISM: Artificial Sequence
<220> FEATURE:
<223> OTHER INFORMATION: Synthetic

<400> SEQUENCE: 55
tttttaaatt taatatgggg atagc                                        25

<210> SEQ ID NO 56
<211> LENGTH: 25
<212> TYPE: DNA
<213> ORGANISM: Artificial Sequence
<220> FEATURE:
<223> OTHER INFORMATION: Synthetic

<400> SEQUENCE: 56
agacgtctta tgttgtaatt attat                                        25

<210> SEQ ID NO 57
<211> LENGTH: 25
<212> TYPE: DNA
<213> ORGANISM: Artificial Sequence
<220> FEATURE:
<223> OTHER INFORMATION: Synthetic

<400> SEQUENCE: 57
acgattgggg actttaattg ggagt                                        25

<210> SEQ ID NO 58
<211> LENGTH: 25
<212> TYPE: DNA
<213> ORGANISM: Artificial Sequence
<220> FEATURE:
<223> OTHER INFORMATION: Synthetic

<400> SEQUENCE: 58
actactcgat tatcaacgtc aagga                                        25

<210> SEQ ID NO 59
<211> LENGTH: 25
<212> TYPE: DNA
```

<213> ORGANISM: Artificial Sequence
<220> FEATURE:
<223> OTHER INFORMATION: Synthetic

<400> SEQUENCE: 59
gtcgcaggac gcctagttct aggaa                                              25

<210> SEQ ID NO 60
<211> LENGTH: 25
<212> TYPE: DNA
<213> ORGANISM: Artificial Sequence
<220> FEATURE:
<223> OTHER INFORMATION: Synthetic

<400> SEQUENCE: 60
aatgggggaa gtttgttgga gttga                                              25

<210> SEQ ID NO 61
<211> LENGTH: 24
<212> TYPE: DNA
<213> ORGANISM: Artificial Sequence
<220> FEATURE:
<223> OTHER INFORMATION: Synthetic

<400> SEQUENCE: 61
agataagttc gctgtattcg gtgt                                               24

<210> SEQ ID NO 62
<211> LENGTH: 25
<212> TYPE: DNA
<213> ORGANISM: Artificial Sequence
<220> FEATURE:
<223> OTHER INFORMATION: Synthetic

<400> SEQUENCE: 62
gaggcattgt tcacgtcgtt tgtta                                              25

<210> SEQ ID NO 63
<211> LENGTH: 25
<212> TYPE: DNA
<213> ORGANISM: Artificial Sequence
<220> FEATURE:
<223> OTHER INFORMATION: Synthetic

<400> SEQUENCE: 63
tgtaaagaat gcgtagagat aggag                                              25

<210> SEQ ID NO 64
<211> LENGTH: 37
<212> TYPE: DNA
<213> ORGANISM: Artificial Sequence
<220> FEATURE:
<223> OTHER INFORMATION: Synthetic

<400> SEQUENCE: 64
aacataagaa cagggaggtt agaagtaggg tcttggt                                 37

<210> SEQ ID NO 65
<211> LENGTH: 25
<212> TYPE: DNA
<213> ORGANISM: Artificial Sequence
<220> FEATURE:
<223> OTHER INFORMATION: Synthetic

<400> SEQUENCE: 65
aaggttgtag tgatgggggt gttta                                              25

<210> SEQ ID NO 66
<211> LENGTH: 25
<212> TYPE: DNA
<213> ORGANISM: Artificial Sequence
<220> FEATURE:
<223> OTHER INFORMATION: Synthetic

<400> SEQUENCE: 66
ttataataat ctttgtgttt tcggc                                              25

<210> SEQ ID NO 67
<211> LENGTH: 25
<212> TYPE: DNA
<213> ORGANISM: Artificial Sequence
<220> FEATURE:
<223> OTHER INFORMATION: Synthetic

<400> SEQUENCE: 67
tatgaagaat agagcgaaga ggcct                                              25

<210> SEQ ID NO 68
<211> LENGTH: 25
<212> TYPE: DNA
<213> ORGANISM: Artificial Sequence
<220> FEATURE:
<223> OTHER INFORMATION: Synthetic

<400> SEQUENCE: 68
gcggcctatt ccatgttgac gcctg                                              25

<210> SEQ ID NO 69
<211> LENGTH: 19
<212> TYPE: DNA
<213> ORGANISM: Artificial Sequence
<220> FEATURE:
<223> OTHER INFORMATION: Synthetic

<400> SEQUENCE: 69
ttcggcaatg tcgaggggg                                                     19

<210> SEQ ID NO 70
<211> LENGTH: 25
<212> TYPE: DNA
<213> ORGANISM: Artificial Sequence
<220> FEATURE:
<223> OTHER INFORMATION: Synthetic

<400> SEQUENCE: 70
gttcggttgg tttttgctgg tgtgg                                              25

<210> SEQ ID NO 71
<211> LENGTH: 25
<212> TYPE: DNA
<213> ORGANISM: Artificial Sequence
<220> FEATURE:
<223> OTHER INFORMATION: Synthetic

<400> SEQUENCE: 71
agataaacca tagtatgtcc gaggg                                              25

<210> SEQ ID NO 72
<211> LENGTH: 25
<212> TYPE: DNA
<213> ORGANISM: Artificial Sequence
<220> FEATURE:

-continued

```
<223> OTHER INFORMATION: Synthetic

<400> SEQUENCE: 72
tcatgattgc agtagtggta agagg                                              25

<210> SEQ ID NO 73
<211> LENGTH: 25
<212> TYPE: DNA
<213> ORGANISM: Artificial Sequence
<220> FEATURE:
<223> OTHER INFORMATION: Synthetic

<400> SEQUENCE: 73
ttgatcaagg ggtttggtat aggga                                              25

<210> SEQ ID NO 74
<211> LENGTH: 25
<212> TYPE: DNA
<213> ORGANISM: Artificial Sequence
<220> FEATURE:
<223> OTHER INFORMATION: Synthetic

<400> SEQUENCE: 74
gggaggttta tagtaaaaga gagat                                              25

<210> SEQ ID NO 75
<211> LENGTH: 24
<212> TYPE: DNA
<213> ORGANISM: Artificial Sequence
<220> FEATURE:
<223> OTHER INFORMATION: Synthetic

<400> SEQUENCE: 75
aatgtgaaat ctgcttgggc tggt                                               24
```